United States Patent [19]

Kushner et al.

[11] Patent Number: 5,089,397
[45] Date of Patent: Feb. 18, 1992

[54] SUPERIOR MAMMALIAN EXPRESSION SYSTEM

[75] Inventors: Peter J. Kushner, San Francisco; Claire L. Cofer, Fremont; Jeffrey S. Friedman; Karen D. Talmadge, both of Palo Alto, all of Calif.

[73] Assignee: California Biotechnology Inc., Mountain View, Calif.

[21] Appl. No.: 366,342

[22] Filed: Jun. 14, 1989

Related U.S. Application Data

[63] Continuation of Ser. No. 801,674, Nov. 25, 1985, abandoned, which is a continuation-in-part of Ser. No. 701,296, Feb. 13, 1985, abandoned.

[51] Int. Cl.$^5$ .................... C12P 21/00; C12N 15/06; C12N 15/00; C12N 15/11
[52] U.S. Cl. .................. 435/69.1; 435/172.3; 435/240.2; 435/320.1; 435/240.1; 536/27; 935/32; 935/34; 935/70
[58] Field of Search .......... 435/68, 70, 71, 91, 435/172.1, 172.3, 240.1, 240.2, 243, 320, 948, 69.1-69.8; 514/2; 536/27; 530/324, 350; 935/9-14, 27, 32, 34, 36, 66, 70, 71, 6

[56] References Cited

U.S. PATENT DOCUMENTS

| | | | |
|---|---|---|---|
| 4,399,216 | 8/1983 | Axel et al. | 435/6 |
| 4,601,978 | 7/1986 | Karin | 435/68 |
| 4,703,008 | 10/1987 | Lin | 435/240.2 |

FOREIGN PATENT DOCUMENTS

8402534  5/1984  PCT Int'l Appl. .............. 435/172.3

OTHER PUBLICATIONS

Richards et al.; Cell 37: 263 (1984).
Searle et al.; Molecular Cell Biology 4: 1221 (1983).
Karin et al.; Nature 299: 797 (1982).
Ringold et al.; J. Mol. Appl. Genet. 1: 165 (1981).
White et al.; Nature 317: 361 (1985).
Huang; Proc. Natl. Acad. Sci. U.S.A. 81: 2708 (1984).
Imai et al.; Proc. Natl. Acad. Sci. U.S.A. 80: 7405 (1983).
Seidman et al.; Science 226: 1206 (1984).
Nakayama et al.; Nature 310: 699 (1984).
Sharpe et al.; Nucleic Acids Res. 12: 3917 (1984).
Shoulders et al.; Nucleic Acids Res. 11: 2827 (1983).
Benoist, C., et al., Nature (1981) 290:304-310.
Brinster, et al., Nature (1982) 296:39-42.
DeNoto, et al., Nucleic Acids Res. (1981) 9:3719.
Goeddel, D. V., et al., Nature (1979) 281:544-548.
Gruss, P., et al., Proc. Natl. Acad. Sci (U.S.A.)(1981) 78:943-947.
Hamilton, W. G. et al., In Vitro (1977) 13:537-547.
Karin, M., et al., DNA (1984) 3:319-325.
Karin, M., et al., Nature (1984) 308:513-519.
Karin, M., et al., Proc. Natl. Acad. Sci. (U.S.A.) (1983) 80:4040-4044.
Kaufman, R. J., et al., Mol. Cell Biol. (1985) 5:1750-1759.
Martial, J. A., et al., Science (1979) 205:602-607.
Mathis, D. J. et al., Nature (1981) 290:310-315.
McCormick, et al., Molec. Cell Biol. (1984) 4:166-172.
Pavlakis, G. N., et al., Proc. Natl. Acad. Sci. (U.S.A.) (1983) 80:397-401.
Wasylyk, B., et al., Nucleic Acids Res. (1984) 12:5589-5608.

Primary Examiner—James Martinell
Attorney, Agent, or Firm—Irell & Manella

[57] ABSTRACT

An expression system for recombinant production of a desired protein comprises CHO cells transformed with a DNA sequence having the desired protein coding sequence under control of the human metallothionein-II promoter. The cells can be maintained on serum-free medium and induced in the presence of an induction mediator. In addition, the system may include an enhancer element and/or a resistance-conferring gene to provide increased levels of expression. The system can process genomic as well as intronless DNA, and is capable of producing proteins which have the same characteristics as those obtained from native sources. Human growth hormone which is indistinguishable from that produced by the pituitary has been thus produced.

37 Claims, 22 Drawing Sheets pMT:PSAP

... ggctcttttctagc[tataaa]cactgcttgccgc
                              → MT-IIA      951
ctgcactccaCACGGCCTCCTCCAAGTCCCAGCGAACCCGTGCAACCTGTCCCGACTCTAGCCGCCTCTTCAGCTCAC GGATCAGTC 1000
PSAP →
CTGACAGAGCACAGTGGGGGAGATGTTGGCAGAGGTGGCAGATGGCTCACGGCAGGAGACAGGAGACTGGACCCAGAGCC
MetLeuAlaGluValAlaAspGlyLeuThrAlaIleProProAlaGlyAlaAlaThrGlyProArgAla
-43

1050                                           1100
ATGTGGCTGTGCCCTCAACCTCATCTTGATGGCAGCCTCTGGTGCTGTGTGCGAAGTGAAGGAGACGTTTGTGTTGGAAGCCCT
MetTrpLeuCysProLeuAlaLeuAsnLeuIleLeuMetAlaAlaSerGlyAlaValCysGluValLysGluValCysValGlySerPro 1150                                    1200
GGTATCCCCGGCACTCCTGGATCCCAGCAGGACACGGAGAGAGATGGTCTCAAAGGAGACCTGGGCCCTCCAG gtact
GlyIleProGlyThrProGlySerHisGlyLeuProGlyArgHisGlyLeuProGlyLeuLysGlyLeuProGlyProGly 1250                                 1300
gtgctgcagaccccaccctcagctgaggacacagacccctttcaggaggccatctgtccaggcccctaggctgtgggcatagtgagc 1350                                 1400
tgggggctatagtaagctgggtgggacttcagtctgcagggctgtggttcctgggcccttatgatggcatcctggagagtctgtc 1450                                 1500
ctcataggtgccacggagtgatagagtgaccagccctggtgataatgggcatcgagtctcactagctccaaccagttgtgg 1550
tgacagatcctacacatccatgtctctttttctctgcag GCCCCATGGGTTCCACCTGGAGAAATGCCATGTCCTCCTGGAAATGATGGG
                                        lyProMetGlyProProGlyGluMETProCysProProGlyAsnAspGly 1600                                    1650
CTGCCTGGAGCCCCTGGTATCCCCTGGAGAGTGTGGAGAGAAGAAGGGGAGCCTGGCAGGGGCCCTCCAG gtgagcagggtggggcagg
LeuProGlyAlaProGlyIleProTrpArgValTrpArgGluGluGlyGluProGlyArgGlyProProGly 1750
tgggcagtggaaacatggcacagcgacctgaagtcagttacacgggatcagtgatgggatcagacaaacctacaggttcccaagggca 1850
tttggctcaacctaagtaagagagagataagcttgaggaggaaagctgaggtgtctgggagtgtggtcacaattcaggaaaggcaggtg 1900
tgggaagtcctccgtgcctcatgaccaccgatggggacactgagtcaggtgggatcaggtgtgaggagacactggaggaggcagggaggcat 1950                                    2000
gtcctgggatgaggcccttgggctgtctgaagggtgaatgcggacgaggcatccagacagacgtgatcaggagccccacagacaga

FIG. 4a

```
                                           2100
                   2050
ggggaactttgaagctcagagcggtaagcggtcatcagggcagtgcagagagcatatgctgccctttcggtcggagggtgcgggaga
              2150                                     2200
gggacttgccccacagagggcgggcagacagaacccctcgaggacagaagacaggggtggggtctcagcaggggcaag
                    2250                                              2300
gcttcactaaagaataggggaccacgggtctgagacacactggaatcttgtggaccctctgagcttggtctggtggcgcctaacagcaa
                              2350
tgaagggcagagttccaggattgcagatgcaaaacacctcgtggcagcaagtgggagtcttcactgctgccctcctctctgtggg
                                     2450
               2400                                                          2500
gcactctccacag GGCTTCCAGCTCATCTAGATGAGGAGGCTCCAAGCCACACTCCAGACTTTAGACATCAAATCCTGCAGACAAGGGAG
              lyLeuProAlaHisLeuAspGluLeuLeuGlnAlaThrLeuHisAspPheArgHisGlnIleLeuGlnThrArgGlyA
                     2500                                     2550
gtaaggggaccccctgggctcacgggtaggagtttcccacaaattccctcattctcagcaccagcttctagaacatagagattacaaa
                                2600                                     2650
taggcatgcacatgcagtctctgggaaaggaattgacgcttgctttttctgatgtcttttgaatggccagaggagacagaagcagaca
                    2700                                              2750
caattcacttcccgatttcatagaaagcaagttctctatccgcctgctcttccactgaattcacaggaaattgcaccattctggcaa
                        2800
taagtaattgttacttaggtgaatgaataaatggaggagtctaaaagtgaatttagaaaactgcaattggaagaggaagagaagacac
                       2850                       2900
agagagagcagagatggagagactggtagcagagaacccagtgagggaggtggcttagagacaaagtggtcagtggc
           2950                                                       3000
ctgacccgactcctctgctctcag CCCTCAGTCTGCAGGGCATGTGCCAGAGAGCAGGCGGGCAGGAGGAGCAGGTCTTCTCCAGCAATGGGCAGTCC
                          laLeuSerLeuGlnGlySerIleMETThrValGlyGluLysValPheSerSerAsnGlyGlnSer
                                    3050                                     3100
ATCACTTTTGATGCCATTCAGGAGGAGCATGTGCCAGAGAGCATGTGTGCCAGAGAGCAGGAAAATGAGGCCATTGCA
IleThrPheAspAlaIleGlnGluGluHisGluLeuLeuLeuLeuLeuLeuLeuLeuLeuLeuLeuLeuLeuLeuLeuLeuLeuLeu
```

FIG. 4b

```
                                                    3350
AGGAACTGCCTGTACTCCCGACTGAGTCTGTGAGTTCTGA GAGGCATTTAGGCCATGGGACAGGGAGGAGACGCTCTCCTTGTCGGCCT
ArgAsnCysLeuTyrSerArgLeuThrIleCysGluPhe .
                                  ←——— PSAP  3435   ApoA1 ———→
                     3400
CCATCCTGAGGCTTCCACTTGGTCTCTGTGAGATGCTAGAAACTCCCTTTCAACA GAATTGATCCCT GCTGCCCGTGCTGGAGAGCTTCAAG

GTCAGCTTCCTGAGGCGCTCTCGAGGAGTACACTAAGAAGAGCTCAACACCCAGTGAGGCGCCGCCGCCCCCCTTCCCGGTGCTCAGAA

TAAAcGTTTCCAAAGTGggaagcagctttcttct...
```

FIG. 4C  pMT-Apo:gHS(HinfI/EcoRI)

pMT(E):HS

... ggctctttctagc[tataaa]cactgctgccgcgctgcactccaCACGCCTCCTCCAAGTCCCAGGAACCCGCTGCAACCTGT
           ──── MT-IIA  2  HS ─────▶                                              50
              GGATCAATTC CCAAGTCGCTGGAGGCTCTGTGTGTGGGAGCAGCGACTGGACCCAGAGCC
CCCGACTCTAGCCGCCTCTTCAGCTCAC ATGTGGCTGTGCCCTCTGGCCCTCAACCCTCATCTTGATGGCAGCCTCTGGTGTGTGCAAGTGAAGGACGTTTGTGTTGGAAGCCCT
METTrpLeuCysProLeuAlaLeuAsnLeuIleLeuMETAlaAlaSerGlyAlaValCysGluValLysAspValCysValGlySerPro
-20                                     100
                       150                                                      1
GGTATCCCCGGCACTCCTGGATCCCACGGCCTGCCAGGCAGGGACGGGAGAGATGGTGTCAAAGGAGACCCTGGCCCCTCCAGGCCCCATG
GlyIleProGlyThrProGlySerHisGlyLeuProGlyArgAspGlyArgAspGlyValLysGlyAspProGlyProProGlyProMET
                                                    200                          *

GGTCCACCTGGAGAAATGCCATGTCCTCCTGGAAATGATGGCCTGCCTGGGCTGGTATCCCTGGAGGTGTGGAGAGAAGGGGAG
GlyProProGlyGluMETProCysProProGlyAsnAspGlyLeuProGlyLeuProGlyIleProGlyGluCysGlyGluLysGlyGlu
           250                                     300                           *

CCTGGGCTTCCAGGCTCATCTAGATGAGGAGCTCCAAGCCACACTCCAGGACTTTAGACATCAAATCCTGCAG
ProGlyLeuProGlyLeuProAlaHisLeuAspGluGluLeuGlnAlaThrLeuGlnAlaThrLeuHisAspPheArgHisGlnIleLeuGln
                   350                                     400

FIG.5a

```
                                                                                                                                                                500
ACAAGGGGAGCCCTCAGTCTGCAGGGCTCCATAATGACAGTAGGAGAGAAGGTCTTCTCCAGCAATGGGCAGTCCATCACTTTGATGCC
ThrArgGlyAlaLeuSerLeuGlnGlyGlySerIleMETThrValGlyGlyGluGluLysValPheSerSerAsnGlyGlnSerIleThrPheAspAla

ATTCAGGAGGCATGTGCCAGGAGCAGGCGGCCGCATTGCTGTCCCAAGGAATCCAGAGGAAAATGAGGCCATTGCAAGCTTCGTGAAGAAG
IleGlnGluAlaCysAlaArgAlaGlyGlyArgIleAlaValProGluAsnProArgAsnProGluGluAsnGluAlaIleAlaSerPheValLysLys
                                                  550
TACAACACATATGCCTATGTAGGCCTGACTGAGGGTCCCAGCCCTGAGACTTCCGTACTCAGACGGGACCCCTGTAAACTACACCAAC
TyrAsnThrTyrAlaTyrValGlyLeuThrGluGlyProSerProGluThrSerValLeuArgArgAspProCysLysLeuHisGln
                             600                                                                650
TGGTACCGAGGGGAGCCCGCAGGTCGGGGAAAAGAGCAGTGTGGAGATGTACACAGATGGGCAGTGGAATGACAGGAACTGCCTGTAC
TrpTyrArgGlyGluProAlaGlyArgGlyLysGluGlnCysValGluMETTyrThrAspGlyGlnTrpAspAsnArgAsnCysLeuTyr
                                                                                                                                                                750
TCCCGACTGACCATCTGTGAGTTCTGAGAGGCATTTAGGCCATGGGACAGGGAGGACGCTCTCTGGCCTCCATCCTGAGGCTCCACTGG
SerArgLeuThrIleCysGluPhe
                                                                                                ← HS   900    ApoA1 →
                                                                                                                                                                      850
TCTGTGAGATGCTAGAACTCCCTTTCAACA GAATTGATCCCT GCTGCCCGTGCTGGAGAGCTTCAAGGTCAGCTTCCTGAGCGCTCTC

TCGAGGAGTACACTAAGAAGCTCAACACCCAGTGAGGCGCGCCCCCTTCCCGGTGCTCAGAATAAACGTTTCCAAAGTGgga...
```

FIG.5b pASPc-SV(10)

FIG.6a

```
... ggctctttctagctagctataaacactgttgccgcgctgcactccaCACGCCTCCTCCAAGTCCCAGTCCCGTGCAACCTGT
                      ← MT-IIA    HS →
CCCGACTCTAGCGCCCTCTTCAGCTCAC GGATCAATTC CCAAGTGCTGGAGGCTCTGTGTGTGGGAGCAGGACTGGACCCAGAGCC
                                         100
ATGTGGCTGTGCCTCTGGCCTCAACCTCATCTTGATGGCAGCCCTCTGGTGCTGTGCGAAGTGAAGGAGACGTTTGTGTTGGAAGCCCT
METTrpLeuCysValalaLeuAlaLeuAsnLeulIleLeuMETAlaAlaSerGlyAlaValCysGluValCysValGlySerPro
-20
        ← HS      PSAP →                                      1200
GGTATCCCCGGCACTCCT GGATCC CACGGGCTGCCCAGGCAGGCACGGGAGAGATGGTCTCAAAGGAGACCTGGGCCCTCCAG gtact
GlyIleProGlyThrPro GlySer HisGlyLeuProGlyArgHisGlyLeuProGlyArgAspGlyArgAspGlyLeuLysGlyAspLeuGlyProProG
     1250                                                              1300
gtgctgcagacccaccctcagctgaggacagagacccctttcaggaggcccatctgtccaggccccctaggctgtgggccatagtgagc
                             1350                                  1400
tggggctatagtaagctggtggacttcagtctgcagggctggtgggttcctgggcctatgatggcgcatcctggagagtctgtc
                                         1450
ctcatagtgccacggagtgatagagtgagccagccagccctggtgataatgggcatcgagtctcactagctccaaccagtgtggg
                                1500                              1550
tgacagatcctacacatcatgtctctcttttctctgcag GCCCATGGGTCCACCTGGAGAAATGCCATGTCCTCCTGGAAATGATGGG
                                       lyProMETGlyProProGlyGluMETProCysProProGlyAsnAspGly
                                                                          1650
CTGCCTGGAGCCCCTGGTATCCCTGGAGAGTGTGGAGAGAAAGGGGAGCCTGGCGAGAGGGGCCCTCCAG gtgagcagggtggggcagg
LeuProGlyAlaProGlyIleProGlyGluCysGlyGlyGluLysGlyGluProGlyGluArgGlyProProG
            1700                                    1750
tgggcagtggaaacatgggcacagcagacccctgaactgaagtcagttacacgggggacacacctgaagtgtgggatcagacaaacctacagttcccaagggca
                              1800                              1850
tttggctcaacctaagtaagaggaggataagcttgagggagaaagctgaggtgtctgggagtggtgtcacaattcagggaaggcaggtg
                                          1900
tgggaagtccctccgtgcctcatgaccaccgatgggacaccactgagtcaggtgtgggatcaggtgtgggatcaggtgggatggagcagtggaggaggcat
                                      1950                                      2000
gtcctggatgggcccctgggccctgtctgaagggtgaatgcgaggacgaggcatccagacgaggtgatcaggagcccacagacaga
                                                2050                              2100
ggggaactttgaagctcagagcggtaagcaagtcagagagcatcatgctgccctttcggtcggagggtgcgggaga
```

FIG.6b

```
                                                                                          2200
                                    2150
gggacttgccccacagagagcgggcagacagaaccccctcgaggacaagacaggaaagaggacaaggggtggggtctcagcaggggcaag
                                                                           2300
                        2250
gcttcactaaagaataggggaccacggggtctgagacacactggaatcttgtggacccctcgagcctaggtcttgtggcgcctaacagcaa 2350
tgaaagggcagagttccaggattgcagatgcaaaacacctcgtggcagcaagtgggagtcttcactggcctgcccctcttctgtgggg
         2400                                                          2450
gcactctccacag GGCTTCCAGTCTCATCTAGATGAGGAGCTCCAAGCCACTCCACGACTTTAGACATCAAATCTGCAGACAAGGGAG
              lyLeuProAlaHisLeuAspGluGluLeuGlnAlaThrLeuAspPheArgHisGlnIleLeuGlnThrArgGlyA 2500                                                      2550
gtaaggggaccccctgggctcacggggtaggagttttcccacaaattccctcattctcagcaccagcttctagaacatagagattacaaa
                           2600                                                 2650
taggcatgcacatgcaggtcttggggaaaggaattgacgcttgctttctgatgtcttttgaatgcccagaggagacagaagacagaca 2700                                                      2750
caattcacttccccgatttcatagaaagcaagttctctatctgccttgctccactgaattcacaggaaaattgcaccattctctggcaa 2800
taagtaattgttacttaggtgaataatgaggagagtctaaaagtgaatttagaaaactgcaattggaagaggaagaagacac
                      2900
agagagagcagagatggagagactggggagaatctggtagcagagaccccagtgagggaggtggcttagagacaaagtggtcagtggc
           2950                                                          3000
ctgacccggactcctctgctctcag CCCTCAGTCTGCAGGGCTTCCATAATGACAGTAGGAGAGAAGGTCTTCTCCAGCAATGGGCAGTCC
                          laLeuSerLeuGlnGlySerIleMETThrValGlyGlyArgArgAsnProGluGluAsnGlyGlnSer 3100
ATCACTTTTGATGCCATTCAGGAGGCATGTGCCAGAGCAGGCCGCATTGCTGTCCCAAGGAATCCAGAGAACTTCCAGGACTTCAGCA
IleThrPheAspAlaIleGlnGluAlaCysAlaArgAlaGlyArgIleAlaValProArgAsnProGluGluAsnPheGlnAspPheSerAla 3200
AGCTTCGTGAAGAAGTACACAACATATGCCTATGTAGCCTATGTGTATGCCTATGTGGAGGTCTCCAGCCCTGACTGCCTACTCAGACGGGACCCCT
SerPheValLysLysTyrAsnThrTyrAlaTyrValGlyLeuThrGlyLysGluProSerProGlyAspPheSerAspArgTyrSerAspGlyThrPro 3250
GTAAACTACCACCAACTGGTACGAGGGGAGCCCGCAGGTCGGGGAGGGAAAAGAGCAGTGTGTGGAGATGTACACAGATGGGCAGTGGAATGAC
ValAsnTyrThrAsnTyrArgGlyArgGlyLysGluProAlaGlyArgGlyLysGluGlnCysValGluMETTyrThrAspGlyGlnTrpAsnAsp
```

```
              3300                                          3350
AGGAACTGCCTGTACTCCCGACTGACCATCTGTGAGTTCTGA GAGGCATTTAGGCCATGGGACAGGGAGGAGGACGCTCTCCTTGTCGGCCT
ArgAsnCysLeuTyrSerArgLeuThrIleCysGluPhe .
                                ←——————PSAP        3435                    ApoA1——————→
              3400              CCAACA GAATTGATCCCT GCTGCCCGTGCTGGAGAGCTTCAAG
CCATCCTGAGGCTCCACTTGGTCTGTGAGATGCTAGAACTCCCTTTCAACA GAATTGATCCCT GCTGCCCGTGCTGGAGAGCTTCAAG

GTCAGCTTCCTGAGGCGCTCTCGAGGAGTACACTAAGAAGCTCAACACCCAGTGAGGCGCCGCGGCCCGCGCCCCTTCCCGGTGCTCAGAA

TAAACGTTTCCAAAGTGggaagcagctttcttct...
```

FIG.6c   pASPcg-SV(10)

```
a                                                              60
ggatccatttgtctcgggctgctggctgcctgccatttcctcctctccacccttatttgg
                                                              120
aggccctgacagctgagccacaaacaaaccaggggagctgggcaccagcaagcgtcaccc
                                                              180
tctgtttccccgcacggtaccagcgtcgaggagaaagaatcctgaggcacggcggtgaga
                                                              240
taaccaaggactcttttttactcttctcacacctttgaagtgggagcctcttgagtcaaa
                                                              300
tcagtaagaatgcggctcttgcagctgagggtctgggggctgttggggctgcccaaggc
                                                              360
agagaggggctgtgacaagccctgcggatgataactttaaagggcatctcctgctggct
                                                              420
tctcacttggcagctttatcactgcaagtgacagaatggggagggttctgtctctcctgc
                                                              480
gtgcttggagagctgggggcttataaaaagaggcggcactgggcagctgggagacaggga
                                                              540
cagacgtaggccaagagaggggaaccagagaggaaccagaggggagagacagagcagcaa
                                                              600
gcagtggattgctccttgacgacgccagcATGAGCTCCTTCTCCACCACCACCGTGAGCT
                             MetSerSerPheSerThrThrThrValSerP
                                                              660
TCCTCCTTTTACTGGCATTCCAGCTCCTAGGTCAGACCAGAGCTAATCCCATGTACAATG
heLeuLeuLeuLeuAlaPheGlnLeuLeuGlyGlnThrArgAlaAsnProMetTyrAsnA
                                                              720
CCGTGTCCAACGCAGACCTGATGGATTTCAAGgtagggccaggaaagcgggtgcagtctg
laValSerAsnAlaAspLeuMetAspPheLys
                                                              780
gggccaggggggctttctgatgctgtgctcactcctcttgatttcctccaagtcagtgagg
                                                              840
tttatccctttccctgtattttccttttctaaagAATTTGCTGGACCATTTGGAAGAAAA
                                  AsnLeuLeuAspHisLeuGluGluLy
                                                              900
GATGCCTTTAGAAGATGAGGTCGTGCCCCCACAAGTGCTCAGTGAGCCGAATGAAGAAGC
sMetProLeuGluAspGluValValProProGlnValLeuSerGluProAsnGluGluAl
                                                              960
GGGGGCTGCTCTCAGCCCCCTCCCTGAGGTGCCTCCCTGGACCGGGGAAGTCAGCCCAGC
aGlyAlaAlaLeuSerProLeuProGluValProProTrpThrGlyGluValSerProAl
                                                              1020
CCAGAGAGATGGAGGTGCCCTCGGGCGGGGCCCCTGGGACTCCTCTGATCGATCTGCCCT
aGlnArgAspGlyGlyAlaLeuGlyArgGlyProTrpAspSerSerAspArgSerAlaLe
                                                              1080
CCTAAAAAGCAAGCTGAGGGCGCTGCTCACTGCCCCTCGGAGCCTGCGGAGATCCAGCTG
uLeuLysSerLysLeuArgAlaLeuLeuThrAlaProArgSerLeuArgArgSerSerCy
```

FIG.7a

```
                                                              1140
CTTCGGGGGCAGGATGGACAGGATTGGAGCCCAGAGCGGACTGGGCTGTAACAGCTTCCG
sPheGlyGlyArgMetAspArgIleGlyAlaGlnSerGlyLeuGlyCysAsnSerPheAr

1200
Ggtaagaggaactggggatggaaatgggatgggatggacactactgggagacaccttcag
g 1260
caggaaagggaccaatgcagaagctcattccctctcaagtttctgccccaacacccagag 1320
tgccccatgggtgtcaggacatgccatctattgtccttagctagtctgctgagaaaatgc 1380
ttaaaaaaaaaaggggggggggctgggcacggtcgtcacgcctgtaatcccagcactttgg 1440
gaggccaggcagcggatcatgaggtcaagagatcaagactatcctggccaacatggtgaa 1500
accccagctctactaaaaatacaaaaattagctgggtgtgtggcgggcacctgtactctc 1560
agctacttgggaggctgaggcaggagaatcacttgaacccaggaggcagaggttgcagtg 1620
agcagagatcacgccactgcagtccagcctaggtgatagagcgagactgtctcaaaaaaa 1680
aaaaaaaaaggccaggcgcggtggctcacgcctgtaatcccagcgctttgggaggccaag 1740
gcgggtggatcacgaggtcaggagatggagaccatcctggctaacacggtgaaaccccgt 1800
ctctactaaaaatacaaaaaattagccaggcgtggtggcaggcgcctgtaagtcctcgct 1860
actccggaggctgaggcaggagaatggcgtgaacccgggaggcggagcttgcagtgagca 1920
gagatggcaccactgcactccagcctgggcgacagagcaagactccgtctcaaaaaaaaa
```

FIG.7b

```
                                                                    1980
aaaaaaaaaaagcaactgccactagcactgggaaattaaaatattcatagagccaagttat
                                                                    2040
ctttgcatggctgattagcagttcatattcctccccagaattgcaagatcctgaagggct
                                                                    2100
taagtgaaatttactctgatgagtaacttgcttatcaattcatgaagctcagagggtcat
                                                                    2160
caggctggggtgggggccggtgggaagcaggtggtcagtaatcaagttcagaggatgggc
                                                                    2220
acactcatacatgaagctgacttttccaggacagccaggtcaccaagccagatatgtctg
                                                                    2280
tgttctctttgcagTACTGAagataacagccagggaggacaagcagggctgggcctaggg
               Tyr
                                                                    2340
acagactgcaagaggctcctgtcccctggggtctctgctgcatttgtgtcatcttgttgc
                                                                    2400
catggagttgtgatcatcccatctaagctgcagcttcctgtcaacacttctcacatctta
                                                                    2460
tgctaactgtagataaagtggtttgatggtgacttcctcgcctctcccacccccatgcatt
                                                                    2520
aaattttaaggtagaacctcacctgttactgaaagtggtttgaaagtgaataaacttcag
                                                                    2580
caccatggacagaagacaaatgcctgcgttggtgtgctttctttcttcttgggaagagaa ttc
```

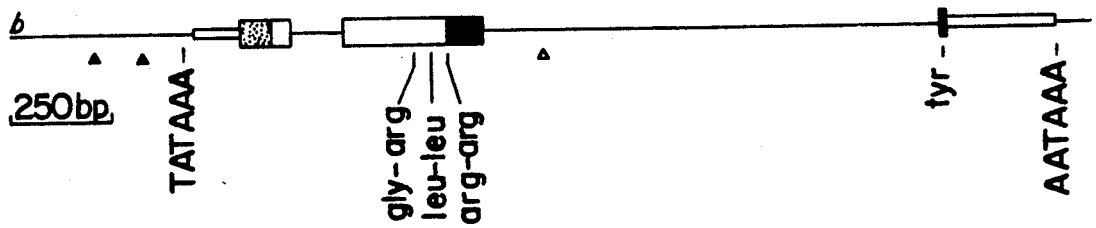

FIG.7c

Distribution of production in following pools

SUPERIOR MAMMALIAN EXPRESSION SYSTEM

This application is a continuation of U.S. Ser. No. 06/801,674, filed 25 Nov. 1985 and now abandoned, which is a continuation-in-part of U.S. Ser. No. 06/701,296, filed 13 Feb. 1985 and now abandoned.

TECHNICAL FIELD

The present invention relates to the expression of desired gene sequences in mammalian expression systems. In part, it relates to a system which utilizes the human metallothionein-II promoter. Chinese hamster ovary (CHO) cellular hosts, which are capable of viability on protein-free medium, and induction in the presence of an induction mediator using relatively non-toxic metals such as zinc ion. Additional improvements in mammalian cell based expression include selection of the transformed host cells for cadmium resistance and/or employing gene amplification techniques and including an enhancer operably linked to the regulatory sequences for gene expression.

The expression system results in gene products encoded by a variety of DNA sequences. The gene products are similar to those from native sources. This similarity is most dramatically shown with respect to human growth hormone (hGH), human alveolar lung surfactant (hASP), and apolipoprotein AI (apoAI).

BACKGROUND ART

Expression of foreign gene sequences using mammalian hosts is, by now, well-known in the art. Mammalian expression systems are often favored because the host cell possesses processing capability which permits modification of gene products, for example by glycosylation or hydroxylation, unlike bacterial, or even yeast systems.

Also, the ability of mammalian systems to secrete certain gene products efficiently into the medium results in easier harvest and purification. Because the secreted product must be purified from other proteins in the medium, it is clearly desirable to employ hosts capable of growth in defined media—i.e., media free from added proteins. While most mammalian cell lines require supplements, such as serum proteins, Chinese Hamster Ovary (CHO) cells can be maintained in defined, serum-free and protein-free medium. (See Hamilton, W. G. and Ham, R. G. *In Vitro* (1977) 13: 537-547). CHO cells are also fast growing and well characterized, free of recognizable dangers, and are thus, in addition to their ability to be maintained serum free, ideal hosts for recombinant protein production.

Mammalian expression, of course, requires compatible control sequences. The most commonly employed control sequences, in particular, promoters, have been viral promoters, most prominently the SV40 promoter (see, for example, EPO Publication 108,667, published 16 May 1984; McCormick, et al, *Molec Cell Biol* (1984) 4: 166-172) or the gene's own promoter, if compatible (U.S. Pat. No. 4,399,216 to Axel, et al). In general, such promoters are less than satisfactory because they cannot be regulated by environmental factors. Absent such control, the linked coding sequences may be expressed at too high or too low a level in the host organism, or at an improper time, and the worker in the art is powerless to control these aspects of expression. Therefore, attempts have been made to utilize mammalian-compatible promoters susceptible to environmental control.

Notable among these promoters are the metallothionein promoters, which natively control the expression of metallothionein proteins—proteins which bind tightly to heavy metals. In their native state, the metallothionein promoters are induced both by the presence of heavy metals, for example, cadmium or mercury, and also by steroid hormones and related materials, such as dexamethasone or other glucocorticoids. However, it has not been possible to carry out induction in the absence of protein-supplemented media, thus limiting the use of such promoters to conditions where purification of the protein produced is complicated by the presence of large amounts of additional contaminants.

Various members of the metallothionein promoter family have been used to control expression in mammalian systems. For example, PCT application WO 84/02534, published July 5, 1984, to Hamer, et al, discloses the use of the mouse metallothionein-I (mMT-I) promoter to control the expression of human growth hormone in mouse kidney C127 cells (see also Pavlakis, G. N., et al, *Proc Natl Acad Sci* (U.S.A.) (1983) 80: 397-401). Brinster, et al, *Nature* (1982) 296: 39-42, obtained thymidine kinase production in injected mouse embryos under control of the murine MT-I promoter. Karin, M., et al, *DNA* (1984) 3: 319-325; *Nature* (1984) 308: 513-519 have studied transient expression under the control of the human metallothionein-II$_A$ system (hMT-II$_A$) in NIH-3T3 cells, by fusing the hMT-II$_A$ promoter to the coding sequences of thymidine kinase to generate hMT-TK chimeric genes, and monitoring expression of TK after deletions in the promoter sequences. Induction was obtained using either cadmium ion, or, in some instances, dexamethasone; and the locations of these regulatory sites were determined by deletion studies.

None of the expression systems disclosed, including those utilizing some form of the MT promoter, permit satisfactory culturing and induction of the host to produce the desired gene product in continuous high yield and in easily recoverable form, free of added serum or other proteins. The expression system of the present invention permits continuous induction of high levels of expression in hosts grown in serum-free medium, and thus permits high levels of protein production and easy purification of secreted products.

In addition to providing non-toxic induction and culture conditions favorable to purification of the desired protein from the medium, it is desirable to enhance the level of production of this protein. Three general approaches relevant to the invention herein have been used to enhance protein production in the past: inclusion of viral enhancers in the expression system, selection of transformed cells for high levels of expression of the transforming DNA, and amplification of the expression system to increase copy number.

Enhancers are cis-acting DNA elements which stimulate transcription. Their activity is relatively independent of their 5'-3' orientation, and, while position dependent to some degree, is retained over distances as long as several thousand nucleotides. Enhancers have been identified in a number of viral genomes and in specialized cellular genes, such as those responsible for the production of immunoglobulins. The enhancer used in the illustration below, which is derived from the simian virus SV40, has been characterized in some detail (Gruss, P., et al, *Proc Natl Acad Sci* (USA) (1981) 78: 943-947; Benoist, C., et al, *Nature* (1981) 290: 304-310; Mathis, D. J., et al, ibid, 310-315). Wasylyk, B., et al,

*Nucleic Acids Res* (1984) 12: 5589-5608 showed that the 72 bp repeat which is thought to be the essential element of the SV40 enhancer has a biphasic dependence on distance from tandem conalbumin promoters linked to the coding sequence for early T antigen used as a diagnostic for transcription enhancement. The invention herein, in some of its aspects, utilizes the stimulating effect of enhancer sequences to increase production levels.

Use of the ability of DHFR to select and to amplify in response to certain drugs to effect an increase in the production of protein by a co-transforming expression system has been practiced for several years. See, for example Kaufman, R. J., et al, *Mol Cell Biol* (1985) 5: 1750-1759. It is believed that relevant selection for high production of desired protein through selection for drug resistance and co-amplification of the desired gene along with DHFR occurs because the DHFR gene and the co-transforming gene are integrated in nearby positions into the chromosome of the host. Thus, local conditions favoring expression are applicable, in general, to both genes. Further, amplification in response to the drug occurs over distances of approximately 200 kb, thus carrying the co-transforming gene along with the DHFR in making multiple copies.

The MT gene has not been used analogously. While the ability of the MT gene to amplify in response to cadmium ion is known, this has been studied using bovine papilloma virus (BPV), a self-replicating transforming system, and therefore use of this amplification to co-amplify a desired expression system has not been suggested (Karin, M., et al, *Proc Natl Acad Sci* (USA) (1983) 4040-4044); nor has cadmium resistance been used as a selectable marker when integrated into the gene to identify high level expressors. In some aspects, the invention herein employs an expression system which takes advantage of an MT gene co-transformed with the expression system either to select for transformants with high level expression abilities for the desired sequence, or to amplify the MT and expression sequences simultaneously, or both.

The various aspects of the invention for improving the quality and quantity of expression in CHO cell hosts are illustrated below for the production of a variety of proteins. In one such illustration the gene for human growth hormone is employed, as this material is of practical interest, of benefit therapeutically, and has not been produced in natural form according to current methods. Recombinant production of hGH, although commonly done, does not result in a product which is true to the mixture of materials produced by the pituitary. Native hGH is a mixture which contains approximately 10% of a minor form, 20 kD hGH, in addition to 90% of the major, 22 kD, species. Both species are encoded by a single gene and result from translation of two different mRNAs produced by differential splicing of the second intron from the primary transcript (DeNoto, et al, *Nucleic Acids Res* (1981) 9: 3719). Hence, production employing cDNA for hGH (EPO Application 108,667 (supra)) or production employing a combination of cDNA and genomic sequences, but lacking the second intron (Hamer, WO84/02534; Pavlakis, *Proc Natl Acad Sci* (supra)) is not satisfactory from this viewpoint, since only the 22 kD form is produced. Even less satisfactory are bacterially produced recombinant hGH preparations (Goeddel, D. V., et al, *Nature* (1979) 281: 544-548; Martial, J. A., et al, *Science* (1979) 205: 602-607) as the hGH thus produced is not secreted into the medium, and at least a major proportion of the hGH produced contains an N-terminal methionine as a result of the recombinant construction and the inability of the host cell further to process the resulting protein.

Significant advantages over, for example, bacterial expression are also seen for hASP. Isolation of hASP from an alveolar proteinosis patient gives a mixture wherein the major species is a 32 kd protein; this indicates that the putatively native form is glycosylated (White, R. T., et al, *Nature* (1985) 317: 361-363). This is also true of canine ASP where similar heterogeneity (28 kd-36 kd) is found. Human cDNA shows an open reading frame encoding 248 amino acids; the sequence beginning at amino acid 21 encoded by this cDNA corresponds to the 22 N-terminal amino acids of the 32 kd protein isolated from lavage fluid. The cDNA has also permitted location of the exon regions of the gene. The cDNA sequence encodes a number of collagen like Gly-X-Y repeats which contain a proline residue. The presence of hydroxyproline in the native sequence indicates these are hydroxylated. Thus, reconstruction of "native" ASP requires at least two post-translational steps available only in mammalian systems—hydroxylation of the proline residues and glycosylation.

Apolipoproteins AI and AII, found in connection with lipids as carriers in the bloodstream are encoded as preproproteins and secreted in "pro" form. However, the protein associated with phospholipids to generate the stacked disc structure of the lipoprotein fractions is mostly mature protein (Boganouski, D., et al, *J Lipid Res* (1985) 26: 185). In this case, too, post-translational modifications of which only mammalian cells are capable, are desirable to generate the native functional form.

The present invention provides not only human growth hormone preparations similar to those produced by the pituitary, human ASP preparations similar to those found in lung lavage fluid, and apolipoproteins functionally associated with phospholipids, but also a means for efficient production and recovery of any desired foreign protein under favorable, high production, easy purification conditions.

DISCLOSURE OF THE INVENTION

An expression system is provided which permits environmental control of expression for foreign gene sequences in a mammalian host that is capable of processing the gene products, to obtain materials in high yield which are virtually identical to the naturally produced substances. The host systems employed are capable of processing intron sequences, so that genomic coding units may be used directly. They are also capable of glycosylation, hydroxylation, "pro" sequence cleavage, or other protein modification after translation, and of processing normally associated signal sequences so that, if desired, the materials are secreted into the medium under conditions where the medium is free of substantial amounts of contaminating protein. The control sequences respond to inducers of low toxicity in the presence of non-protein induction mediators. In addition, the expression system in some embodiments is capable of selection for high expression and of amplification, and may be further modified with enhancers to elevate the levels of production. Thus, the expression system of the present invention provides a host capable of post-translational processing, control of expression, expression at high levels, and ease of purification for the protein produced. This combination of advantages and even subsets thereof are unavailable in the expression systems previously known.

In one aspect, the invention relates to an expression system for any desired coding sequence. The system comprises the mammalian metallothionein-II (hMT-II) promoter operably linked to the coding sequence and transformed into mammalian cells maintained on a defined protein-free medium, particularly CHO cells. Optionally, the system further contains an operably linked enhancer capable of elevating the levels of production and/or a resistance conferring gene capable of effecting amplification of the entire system. The system is induced by a mixture of a non-toxic metal ion in combination with an induction mediator such as iron ion or transferrin.

The invention also relates to methods of expressing genes in mammalian host cells using these expression systems, and to the proteins thus produced. It also relates to methods for selecting recombinant cells capable of high levels of expression and for amplifying a desired expression system by taking advantage of co-transformation with an MT gene and treatment with heavy metal ion.

Another aspect relates to proteins produced in conformity with their native functional forms. In particular, these proteins include human growth hormone recombinantly produced in a form which mimics that natively obtained from the pituitary; hASP which is hydroxylated and glycosylated like that obtained from lavage fluid and apolipoprotein which are obtained in mature form free of pro sequences. These and other preparations which conform to the native proteins can be produced using the methods and expression systems of the invention.

BRIEF DESCRIPTION OF THE DRAWINGS

FIG. 4 is the DNA sequence and deduced amino acid sequence of a construct including the genomic sequence which encodes human alveolar surfactant protein (hASP).

FIG. 5 shows the DNA sequence and deduced amino acid sequence for a construct including cDNA encoding hASP.

FIG. 6 shows the insert containing hASP encoding sequences used to obtain pASPcg-SV(10).

FIG. 7 shows the sequence of the genome encoding human atrial natriuretic factor (hANF).

MODES OF CARRYING OUT THE INVENTION

A. Definitions

Figure 1:
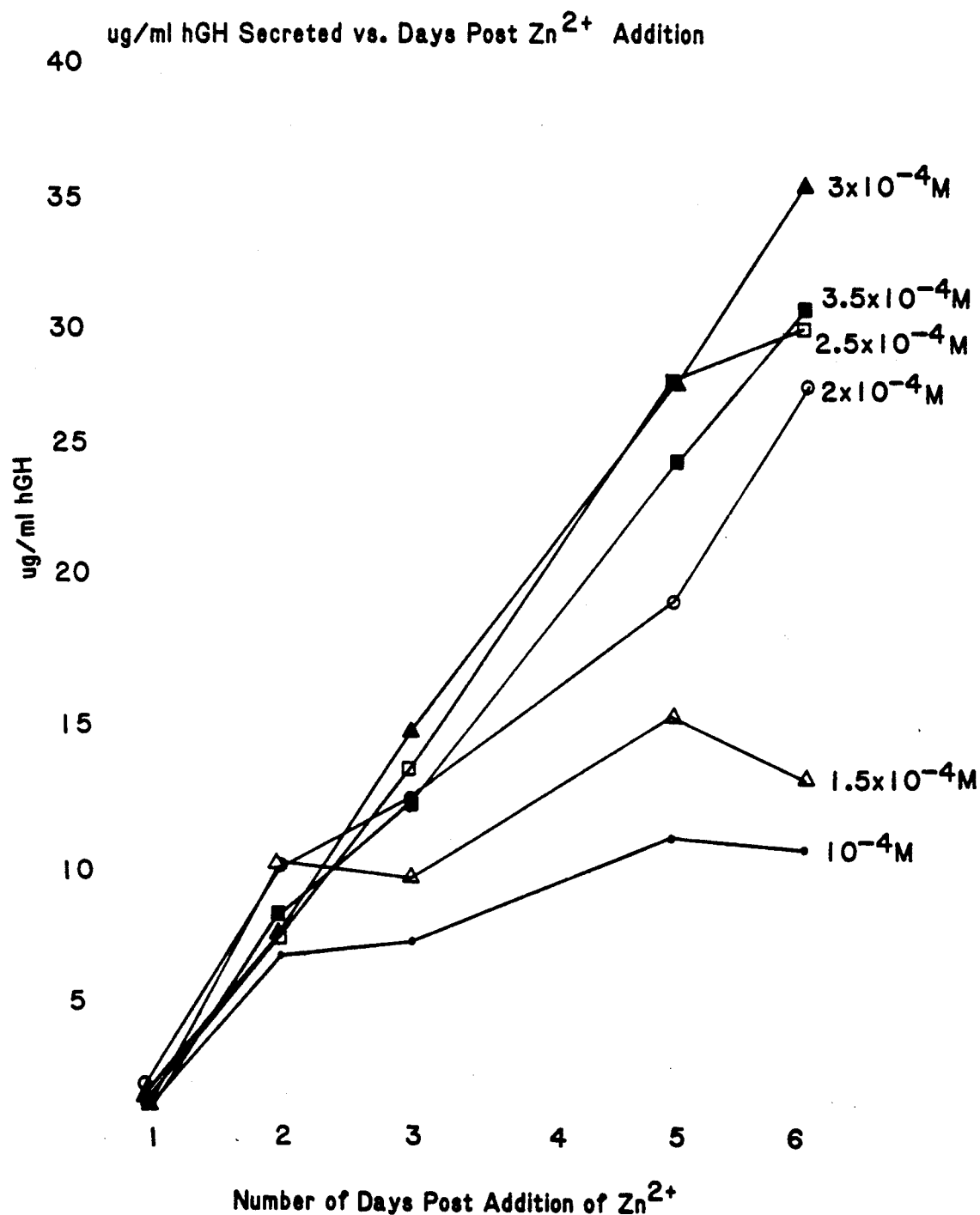
FIG. 1 shows the production of human growth hormone by CBI-37 cells as a function of time, at various zinc ion inducing levels.

As used herein, "operably linked" refers to a juxtaposition such that the ordinary functions of the operably linked materials may be carried out. Thus, a promoter "operably linked" to a coding sequence refers to a configuration wherein the coding sequence can be expressed under control of the promoter in compatible hosts.

"Expression system" refers to a collection of components as subsequently designated and may include, as specified, only a coding sequence operably linked to control sequences, to these sequences further linked to an enhancer, to a vector containing these, to cells transformed by the vector, or to cultures containing the transformants, including medium components.

"Defined medium" refers to a culture medium which has no protein-containing supplements. Most mammalian cell cultures require such supplements. Serum preparations, such as fetal calf serum, in amounts on the order of 10% are ordinarily employed.

"Induction mediator" is a material added, in addition to the metal ion inducing the MT promoter, whose presence permits this induction to occur in defined medium. In the context of the expression system of the present invention, it has been found that iron (ion) in concentrations of $1-3\times10^{-5}$M or transferrin at 5 µg/ml or more behave as induction mediators. Iron ion is most conveniently provided as iron (II) since iron (III) tends to precipitate. However, iron (III) can also function as an induction mediator. While the transferrin is an iron-containing protein, the amounts required for its function as an induction mediator are much smaller than those used for protein supplements. Therefore, it does not interfere with purification and is not considered to be a "protein supplement" so as to cause the medium to cease being "defined". Also, it need not be added until induction is initiated.

"Human metallothionein-II" promoter (hMT-II) refers to control sequences derived from the human MT-II gene or their functional equivalents. The control sequences of this gene are described in detail by Karin, M., et al, *Nature* (1982) 299:797–802.

"Host cells", "transformant cells", "cell cultures", "cell lines", and so forth, are used interchangeably herein, as will be clear from the context. Host cells suitable for recombinant transformation refer to cells which have been or are intended to be recipients of new DNA sequences, most commonly in the form of plasmids, but including other transferable DNA forms as well. In this regard, these terms refer not only to the immediate recipient, but also its progeny. Progeny includes product cells of cell division, as well as of other reproductive mechanisms. Progeny includes cells which contain substantially identical DNA sequence content, as well as those wherein the DNA has been altered by accidental or deliberate mutation. It is understood that such mutations may occur as a matter of course in the production of progeny. All progeny which maintain the functionality of the initial transformant, most commonly the ability to produce a specific desired protein, are included in this definition.

"Chinese Hamster Ovary" (CHO) cells include the standard cell line ATCC CCL-61, and its relatives isolated from the same source tissue, as well as derivatives thereof. Derivatives are mutants of the line which may differ genotypically or phenotypically from the original line, but which are obtained therefrom by intentional or inadvertent mutation.

"Derived from" as it pertains to, for example, DNA or protein sequences refers to similarity in structure and not necessarily to physical derivation.

"Amplifiable toxin-resistance conferring gene" refers to a DNA sequence capable of producing (in suitable hosts) a protein which confers resistance on the host to an otherwise toxic element placed in the host's environment and which gene may be produced in multiple copies in the presence of this toxic element. "Toxin" here refers to any material which is deleterious to the host at the concentration levels supplied. Appropriate exemplary toxins are drugs such as methotrexate, to which DHFR confers resistance, and $Cd^{+2}$, to which the MT protein confers resistance. Both the DHFR and MT genes may respond to the appropriate toxin by amplification, i.e., production of multiple copies.

B. General Description

The present invention offers a substantial improvement in recombinant protein production by virtue of combining particularly favorable conditions for expression in mammalian cells. The metallothionein-II control sequences are advantageously used by virtue of their ability to be inducible by zinc ion, as opposed to the mercury or cadmium ion induction required for MT-I. The latter metals are much more highly toxic to cells, and do not permit, therefore, finely tuned regulation of expression based on regulation of the inducing ion concentration level. In addition to hMT-II illustrated below. MT-II control sequences isolated from other mammalian species may be used. While hMT-II is preferred, MT-II from, for example, bovine, equine, monkey, hamster, porcine, or murine sources is satisfactory. The MT-II genes from mouse, hamster and monkey have been isolated. See, e.g., Searle, P. F., et al, *Mol and Cell Biol* (1984) 4:1221–1230.

In the expression system of the invention, these control sequences are used in cells which are maintained on defined media. An integral feature of the system is addition to the defined medium, as induction mediators, $1-3 \times 10^{-5}$M iron salts or 5 μg/ml or more of transferrin. These additions permit the control sequences to be induced under defined medium conditions. The use of defined medium is a tremendous advantage in production of desired proteins, in that the ability to provide culture conditions wherein the medium does not contain extraneous protein, such as is usually supplied by serum, permits the desired protein to be secreted into a contaminant-free environment.

A useful host expression vector as a component of the expression system is one which contains restriction sites downstream of the MT-II control sequences to permit insertion of a desired coding sequence. Such a vector, illustrated below by pHS1, contains replication sites operable in bacteria, to permit amplification of the host vector and coding sequence insert fragments. The coding sequences ligated into the restriction sites may be either cDNA sequences or genomic fragments containing introns, as the resulting vectors are compatible with hosts capable of processing introns.

Additional improvements may be made to the expression systems by including an operably linked enhancer and/or a toxin-resistance conferring gene, which can select for efficient expression and can stimulate amplification of associated sequences.

Enhancers act in a "cis" manner, and thus need to be included on the same DNA as the remainder of the expression system. Any enhancer sequence from viral or from specialized cells of higher organisms may be used. Viral enhancers have been disclosed which are derived from retroviral long terminal repeats, polyoma virus, Bk virus, and adenovirus, as well as from SV40 as illustrated below. Certain specialized cellular expression systems such as those for ovalbumin and immunoglobulins may also contain enhancer sequences. These enhancers appear to exert their most dramatic effects on relatively weak promoters, and their ability to impact expression controlled by the strong MT-II promoter is surprising. As used in the system of the present invention, the enhancer sequences are ligated within several kb of the promoter regulating the expression of the desired coding sequence, and in either orientation with respect to it. Preferable orientations and distances for the SV40 enhancer are disclosed hereinbelow in connection with the illustrated systems; these preferences are variable depending on the enhancer and regulated system selected. It is believed that for most systems, the SV40 enhancer is most advantageously located 100-400 bp upstream of the start of transcription.

Genes conferring resistance to toxins can be used to select transformants which are effective in expression of foreign, transforming DNAs. The DNA of the expression system for the desired protein can, of course, be associated with the resistance gene by ligating it into the same transfer vector, but this is not necessary in all cases. Since transforming DNA, even from multiple vectors, is often integrated into the genome of its mammalian host to reside in proximal positions, even resistance genes introduced on co-transforming plasmids can be used to select for increased expression of the desired gene. Indeed for cells transformed with modified pHS1 vectors, integration is required as the vector is not self-replicating in mammalian hosts. Any toxin-resistance conferring gene may be used, such as the genes encoding DHFR or MT. The resistance gene preferred in the present improved expression system is the metallothionein gene, which confers resistance to the toxic effects of heavy metals such as cadmium. By selecting transformants in medium containing low levels of cadmium—i.e., up to about 25 μm, individual clones can be selected which have acquired resistance to this toxin concentration, possibly by synthesizing multiple copies of the MT gene, but in any case, by being more effective in producing the metallothionein protein. In such clones, there is a high probability that co-transformed sequences will have integrated at high copy number or reside in a more favorable expression environment as well, and hence will have an increased ability to produce the proteins encoded by them. Cadmium selection of high level expressing clones is surprisingly more effective than with other resistance-conferring genes, such as DHFR or neo, possibly because the cells are exquisitely sensitive to cadmium and certain other heavy metals, and possibly because the toxicity increases linearlly with increasing toxin concentration. Also, unlike with DHFR selection or with standard amplification protocols (Kaufman et al., supra), the cell lines which have been selected on this basis, as illustrated below, appear to retain toxin resistance and high level expression even in the subsequent absence of selective pressure.

Certain resistance-conferring genes, including the MT gene, respond to the presence of the toxin by producing multiple copies both of themselves and of associated DNA. Therefore, in addition to using the MT sequences for initial selection of high level expression, advantage may also be taken of the ability to coax gene amplification in selected cells. This procedure, as outlined, for example, in Kaufman, et al (supra), consists of protracted subculturing in incrementally higher levels of the toxic agent to obtain progressively higher levels of gene copy number. Because of the association between the MT gene and the desired expression system in the transformants, multiple copies of the expression system are obtained using this technique.

The expression vectors, according to the invention, are transformed into host cells which can be maintained on defined medium, although they may have been grown in the presence of serum. Appropriate cells include CHO cells and their derivatives, although any cell line capable of such serum-free maintenance may be used. The transformation may be carried out using a co-transformed antibiotic resistance marker plasmid, either along with or instead of the amplifiable toxin-resistance conferring gene which may also be used as a marker with desired higher expressing cells selected simultaneously. Replication in the host relies on integration of the appropriate sequences into the host genome in the illustration below, but self-replicating vectors may also be used.

The transformed cells are selected for either co-transforming antibiotic resistance or for toxin resistance conferred by a co-transforming amplifiable toxin resistance conferring gene or both. The selected cells are grown in suitable medium, and this growth medium may, if desired, contain serum or other protein supplements prior to induction. (If an amplifiable resistance-conferring gene is included in the system, the transformed cells may also be amplified to high copy number by growing the transformants in increasing concentrations of toxin as described above.) Since the induction of the MT-II promoter is controllable, the medium can be and is exchanged for a defined medium upon induction. Efficient growth is thus permitted while retaining the advantage of a simplified secreted protein purification.

It is of course possible to induce the cells directly in the medium upon which they are grown, using zinc ion in the concentration range of $1-5 \times 10^{-4}$M, approximately. (This concentration range has no definite limits, but amounts within the foregoing arbitrarily set limitations are workable, apparently with an optimum of around $3 \times 10^{-4}$M zinc ion concentration.) However, such direct induction is disadvantageous from the viewpoint of the subsequent protein purification, and it is preferably to exchange the serum-containing medium for basal medium lacking the protein supplement.

Therefore, in the preferred procedure, which is distinctive to the herein invention, this medium replacement is made. The inducing zinc ion (in the range of about $2 \times 10^{-5} - 2 \times 10^{-4}$M) is added along with an induction mediator selected from the group consisting of iron ion and transferrin, an iron-containing protein. When the induction mediator is transferrin, the amount added should be about 5 $\mu$g/ml. Larger amounts can be used, but, of course, are disadvantageous as they add contamination to the medium when protein purification is to be done. The amount of iron ion required, preferably as iron (II), is between $1-3 \times 10^{-5}$M iron. The basal medium itself contains approximately $3 \times 10^{-6}$M iron; however, this is insufficient to permit induction to take place in the absence of serum. Concentrations greater than about $3 \times 10^{-5}$M iron result in precipitation of the iron at the pH under which the cells are grown. Relevant data showing suitable ranges of zinc ion concentration are shown in FIG. 1, which illustrates the effect of various concentration levels on hGH production according to the protocol of example, D.5.a, below.

After induction, the desired coding sequence is expressed under the control of the MT-II promoter in copious amounts and, if provided with a leader sequence operable with the mature protein sequence in mammalian cells, is secreted into the medium. While it is possible to produce proteins internal to the cellular environment using the expression system of the invention, there is no particular advantage in doing so, and the leader sequence ordinarily associated with most secreted mammalian proteins is usually included in the desired coding sequence. In addition, while cDNA sequences may also be used in the expression systems, the ability of this host to utilize and express genomic sequence containing introns is advantageous, and can sometimes be particularly important in permitting production of proteins which mimic those naturally produced.

Any desired coding sequence may thus be expressed using the system of the invention. Natively secreted proteins containing their native leader sequences may be produced to effect secretion of the recombinant form; however, proteins which are normally not secreted may also be provided, using recombinant techniques, with leader sequences compatible with the mammalian cell hosts and with their own amino acid sequences or can be produced intracellularly.

Exemplary of the proteins which may produced using the method of the invention are the hormones, such as human growth hormone or other mammalian growth hormones, insulin, auriculin, and the like, useful for correcting metabolic defects; viral proteins, such as those encoding capsid proteins for hepatitis or foot-and-mouth disease viruses, useful for the production of vaccines; lymphokines, such as lymphotoxin, the interleukins, or the interferons, useful in therapy; or other miscellaneous proteins, such as urokinase, tissue plasminogen activator, or alveolar surfactant protein, useful in the treatment of specified conditions.

The foregoing is, of course, simply an illustrative, very partial list. The coding sequence for any desired protein is workable in the system of the invention.

C. Standard Methods

The methods to obtain coding sequences from cDNA or genomic libraries are generally known in the art and details are available from standard reference sources. These techniques are used to obtain desired coding sequences for insertion into the vectors of the invention. In addition, many desired coding sequences have already been cloned and are obtainable either by oligonucleotide synthesis techniques or from existing vectors. For those sequences which are not thus available the procedures of ¶s C.1 and C.2 may be used.

C.1. cDNA or Genomic Library Production

Human genomic libraries are constructed in λ phage as is known in the art. See, e.g., Maniatis, T., et al, *Cell* (1978) 15:687–701. Alternatively, double-stranded cDNA can be synthesized from mRNA isolated using standard techniques, and prepared for insertion into a plasmid vector such as pBR322 using homopolymeric tailing mediated by calf thymus terminal transferase (Sutcliffe, J. G., *Nucleic Acid Res* (1978) 5:2721–2732). First strand cDNA is synthesized by the RNA-dependent DNA polymerase from Avian Myeloblastosis Virus, by priming with oligo (dT) 12–18 on 5 µg mRNA. The RNA template is then liberated from the nascent DNA strand by denaturation at 100° C. for 5 min, followed by chilling on ice. Second strand DNA is synthesized by using the large fragment of DNA polymerase I of *E. coli*, relying on self-priming at the 3'-end of the first strand molecule, thereby forming a double-stranded hairpin DNA. These molecules are blunt-ended at the open-ended termini, and the hairpin loop is cleaved open with S1 nuclease from *Aspergillus oryzae*. S1 nuclease digestion of the double-stranded cDNA takes place in 300 mM NaCl, 30 mM NaOAc, pH 4.5, 3 mM $ZnCl_2$ for 30 min at 37° C. with 600 units enzyme. The cDNA is extracted with phenol:chloroform, and small oligonucleotides are removed by three ethanol precipitations in the presence of ammonium acetate. This is done as follows: a half volume of 7.5M ammonium acetate and two volumes ethanol are added to the cDNA solution, which is precipitated at −70° C. The blunt-ended, double-stranded cDNA is then fractionated by size using gel filtration through a column (0.3×14 cm) Sepharose 4B (Pharmacia Fine Chemicals, Piscataway, N.J.) or by ultracentrifugation in 5–20% glycerol gradient followed by fractionation of the gradient. cDNA roughly greater than the desired length, e.g., 300 base pairs is retained and recovered by precipitation with 70% ethanol. Short (10–30 nucleotides) polymeric tails of deoxycytosine are added to the 3' termini of the cDNA using a reaction containing 0.2M potassium cacodylate, 25 mM Tris, pH 6.9, 2 mM dithiothreitol, 0.5 mM $CaCl_2$, 200 mM cDTP, 400 µg/ml BSA, and 40 units calf thymus terminal deoxynucleotide transferase for 5 min at 22° C. The reaction is extracted with phenol:chloroform, and small oligonucleotides are removed with three ethanol precipitations in the presence of ammonium acetate.

The tailed cDNA is annealed with a host vector such as pBR322 which has been cleaved with, for example, PstI and tailed with oligo dG. In one operable embodiment 2.5 µg pBR322-dG DNA is annealed with the cDNA at a vector concentration of 5 µg/ml, and the hybrids are transferred into *E. coli* MC1061 by the $CaCl_2$-treatment described by Casadaban, M., et al, *Mol Biol* (1980) 138:179–207.

C.2. Probing cDNA or Genomic Libraries cDNA or genomic libraries are screened using the colony hybridization procedure. Each microtiter plate is replicated onto duplicate nitrocellulose filter papers (S & S type BA-85) and colonies are allowed to grow at 37° C. for 14–16 hr on L agar containing 15 µg/ml tetracycline. The colonies are lysed with 10% SDS and the DNA is fixed to the filter by sequential treatment for 5 min with 500 mM NaOH/1.5M NaCl, then 0.5M Tris HCl (pH 8.0)/1.5M NaCl followed by 2×standard saline citrate (SSC). Filters are air dried and baked at 80° C. for 2 hr.

For nick-translated probe, the duplicate filters are prehybridized at 42° C. for 16–18 hr with 10 ml per filter of DNA hybridization buffer (50% formamide (40% formamide if reduced stringency), 5×SSC, pH 7.0, 5×Denhardt's solution (polyvinyl pyrrolidone, plus Ficoll and bovine serum albumin; 1×=0.02% of each), 50 mM sodium phosphate buffer at pH 7.0, 0.2% SDS, 50 µg/ml yeast tRNA, and 50 µg/ml denatured and sheared salmon sperm DNA).

Samples are hybridized with nick-translated DNA probes at 42° C. for 12–36 hr for homologous species and 37° C. for heterologous species contained in 5 ml of this same DNA hybridization buffer. The filters are washed two times for 30 min, each time at 50° C., in 0.2×SSC, 0.1% SDS for homologous species hybridization, and at 50° C. in 3×SSC, 0.1% SDS for heterologous species hybridization. Filters are air dried and autoradiographed for 1–3 days at −70° C.

For synthetic (15–30 mer) oligonucleotide probes, the duplicate filters are prehybridized at 42° C. for 2–8 hr with 10 ml per filter of oligo-hybridization buffer (6×SSC, 0.1% SDS, 1 mM EDTA, 5×Denhardt's, 0.05% sodium pyrophosphate and 50 µg/ml denatured and sheared salmon sperm DNA).

The samples are hybridized with kinased oligonucleotide probes of 15–30 nucleotides under conditions which depend on the composition of the oligonucleotide. Typical conditions employ a temperature of 30°–42° C. for 24–36 hr with 5 ml/filter of this same oligo-hybridization buffer containing probe. The filters are washed two times for 15 min at 23° C., each time with 6×SSC, 0.1% SDS and 50 mM sodium phosphate buffer at pH 7, then are washed once for 2 min at the calculated hybridization temperature with 6×SSC and 0.1% SDS, air dried, and are autoradiographed at −70° C. for 2 to 3 days.

If the amino acid sequence of the desired protein or nucleotide sequence encoding it in mRNA is known, the DNA for insertion into the host vectors of the invention may be obtained either by synthetic means, or, if vectors containing such sequences are on deposit or available, by cloning such vectors. For synthesis of the coding sequences, alternating sense and anti-sense overlapping single stranded oligonucleotides are prepared, and the alternating sense and anti-sense single stranded portions filled in enzymatically by treating with DNA polymerase and dNTPs. The oligomers are prepared by the method of Efimov, V. A., et al (*Nucleic Acids Res* (1982) 6875–6894), and can be prepared using commercially available automated oligonucleotide synthesizers. Kinasing of single strands prior to annealing or for labeling is achieved using an excess, e.g., approximately 10 units of polynucleotide kinase to 1 nM substrate in the presence of 50 mM Tris, pH 7.6, 10 mM MgCl$_2$, 5 mM dithiothreitol, 1-2 mM ATP, 1.7 pM γ32P-ATP (2.9 mCi/mM), 0.1 mM spermidine, 0.1 mM EDTA.

C.3. Modification of Available Coding Sequences

For sequences from cDNA or genomic DNA which require modifications in order to obtain desired mutant proteins, for example, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

C.4. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM dTT and 5-10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease or exonuclease Bal-31 results in hydrolysis of any single-stranded portion.

Ligations are performed in 15-50 μl volumes under the following standard conditions and temperatures: 20 mM Tris-Cl pH 7.5, 10 mM MgCl$_2$, 10 mM dTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na$^+$ and Mg$^{+2}$ using about 1 unit of BAP or CIP per μg of vector at 60° for about one hour. In order to recover the nucleic acid fragments, the preparation is extracted with phenol/chloroform and ethanol precipitated. Alternatively, religation can be presented in vectors which have been double digested by additional restriction enzyme digestion of the unwanted fragments. The desired sequences are thus recovered from colonies responding to probe.

C.5. Verification of Construction

In the constructions set forth below, correct ligations for plasmid construction are confirmed by first transforming *E. coli* strain MC1061 obtained from Dr. M. Casadaban (Casadaban, M., et al, *J Mol Biol* (1980) 138:179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., J Bacteriol (1972) 110:667). The isolated DNA is analyzed by restriction and/or sequenced by the dideoxy method of Sanger, F., et al, *Proc Natl Acad Sci (USA)* (1977) 74:5463 as further described by Messing, et al, *Nucleic Acids Res* (1981) 9:309, or by the method of Maxam, et al, *Methods in Enzymology* (1980) 65:499.

C.6. Hosts Exemplified

Host strains used in cloning and expression herein are as follows:

For cloning and sequencing, *E. coli* strain MC1061 or HB101 was used.

The cells used for expression are Chinese hamster ovary (CHO) cells which, under the conditions herein described, may be maintained on defined medium.

D. EXAMPLES

The examples below are intended to illustrate the invention but not to limit it.

D.1. Construction of Host Expression Vectors pHS1

Figure 2:
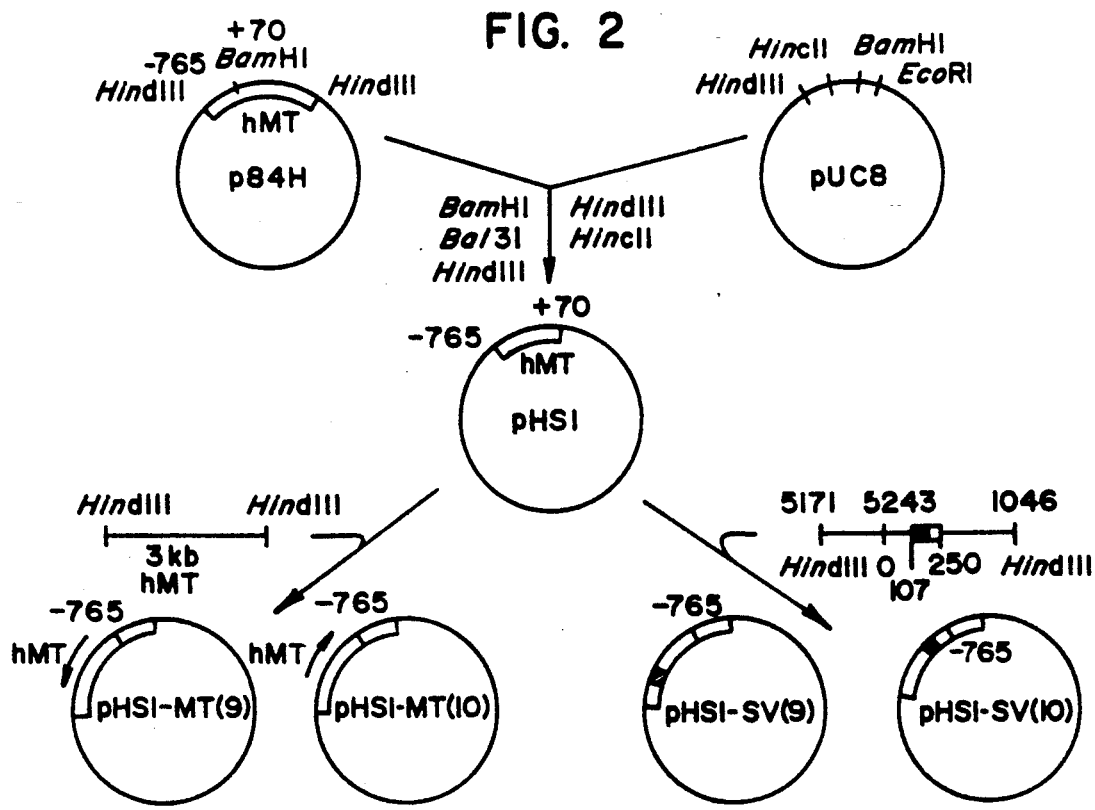
FIG. 2 shows the construction of pHS1, a host expression vector which permits insertion of a coding sequence under control of the hMT-II promoter and of two additional host vectors: pHS1-MT, which contains an expressible metallothionein gene for amplification; and pHS1-SV40, which contains an operably linked SV40 enhancer.

The plasmid pHS1 contains 840 bp of the hMT-II sequence from p84H (Karin, M., et al, *Nature* (1982) 299:797–802) which spans from the HindIII site at position −765 of the hMT-II gene to the BamHI cleavage site at base +70. Plasmid p84H was digested to completion with BamHI, treated with exonuclease Bal-31 to remove terminal nucleotides, and then digested with HindIII. The desired 840 bp HindIII/blunt fragment was ligated into pUC8 (Vieira, J., et al, *Gene* (1982) 19:259–268) which had been opened with HindIII and HincII digestion. The ligation mixture was transformed into *E. coli* HB101 to Amp®, and one candidate plasmid, designated pHS1, was isolated and sequenced by dideoxy sequencing. pHS1, as shown in FIG. 2, contains the hMT-II control sequences upstream of a polylinker containing convenient restriction sites.

pHS1-SV40

A pair of host expression vectors containing the SV40 enhancer in operable linkage to the MT-II promoter was constructed by inserting an 1100 bp SV40 DNA fragment into the HindIII site preceding the MT-II promoter sequences in pHS1. The SV40 DNA fragment spans the SV40 origin of replication and includes nucleotide 5171 through nucleotide 5243 (at the origin), the duplicated 72 bp repeat from nucleotide 107-250, and continues through nucleotide 1046 on the side of the origin containing the 5' end of late viral mRNAs. This HindIII 1100 bp fragment is obtained from a HindIII digest of SV40 DNA (Buchman, A.R., et al, *DNA Tumor Viruses*, 2d ed (J. Tooze, ed.), Cold Spring Harbor Laboratory, New York (1981), pp. 799–841), and cloned into pBR322 for amplification. The cloning vector was cut with HindIII, and the 1100 bp SV40 DNA fragment isolated by gel electrophoresis and ligated into HindIII-digested, CIP-treated, pHS1. The resulting vectors, designated pHS1-SV(9) and pHS1-SV(10), contain the fragment in opposite orientations preceding the MT-II promoter, as shown in FIG. 2. In pHS1-SV(9), the enhancer is about 1600 bp from the 5' mRNA start site; in the opposite orientation it is approximately 980 bp from the 5' mRNA start site. Both orientations are operable, but the orientation wherein the enhancer sequences are proximal to the start site provides higher levels of expression. It is believed that deletions which place the enhancer 100–400 bp upstream of the transcription start are optimal.

pHS1-MT

Host expression vectors containing both the MT-II promoter (to which the desired coding sequences will be ligated) and the entire MT gene were constructed by inserting the 3 kb HindIII fragment containing the entire human metallothionein-II gene (Karin, M., et al, *Nature* (1982) 299:797–802) into HindIII-digested pHS1. The resulting plasmids, pHS1-MT(9) and pHS1-MT(10), contained the entire metallothionein gene 5' of the promoter in each of the two possible orientations. See FIG. 2. Either orientation is operable.

These vectors are particularly useful as host vectors to construct expression vectors for any gene not containing an internal BamHI site, as the BamHI site downstream from the promoter can conveniently be used for insertion. Alternate constructions of the desired expression vectors are utilized, as described below, for, for example, the hGH-encoding sequences, which do contain BamHI sites.

D.2. Construction of MT Vector for Co-transformation

To permit selection or amplification using different starting levels of the expression system and the MT gene conferring cadmium resistance, general shuttle vectors designated pUC9/MT were constructed by ligating the MT-II gene obtained as a HindIII fragment from p84H (supra) into HindIII-digested, alkaline phosphatase-treated, pUC9. Either orientation of the gene is satisfactory.

D.3. Construction of Expression Vectors

The basic expression vector for a DNA-encoding protein X under the control of the MT-II promoter is designated pMT-X. Those vectors in which pMT-X is modified also to contain operably linked SV40 enhancers are generically designated pX-SV40. When the enhancers sequences correspond in location to those in pHS1-SV(9) and pHS1-SV(10)—i.e., 1600 bp or 980 bp from the transcription start site, respectively, the vectors are designated pX-SV(9) or pX-SV(10). Those vectors in which pMT-X is modified to contain the complete MT gene are generically designated pX-MT, again pX-MT(9) and pX-MT(10) indicate analogy to pHS1-MT(9) and pHS1-MT(10).

In all cases, when placed after "X" in the designation, "c" refers to a cDNA insert; "g" refers to a gene.

D.3.a. Vectors for the Expression of Growth Hormone pMT-hGHg

The genomic sequences encoding hGH were isolated from p2.6-3 (DeNoto, et al, *Nucleic Acids Res* (1981) 19:3719) by digestion with BamHI, which cuts at the 5' end of the first exon, and EcoRI, which cuts 3' of the functional gene, followed by polyacrylamide gel purification. The isolated fragment was ligated into BamHI/EcoRI digested pHS1 and the ligation mixture transformed into *E. coli* MC1061 to Amp®. Successful transformants were screened by restriction analysis, and a strain containing the desired plasmid, pMT-hGHg (see FIG. 3) was further propagated to prepare quantities of plasmid DNA.

phGHg-SV40

In a manner similar to that described above for constructing pHS1-SV(9) or pHS1-SV(10), but substituting for pHS1, pMT-hGHg, a pair of vectors containing the hGH gene under the control of the MT promoter, and operably linked to SV40 enhancer, designated, respectively, phGHg-SV(9) and phGHg-SV(10), were obtained. The ligation mixtures were used to transform *E. coli* 1061 to Amp®, and the correct constructions verified.

phGHg-MT

Figure 3:
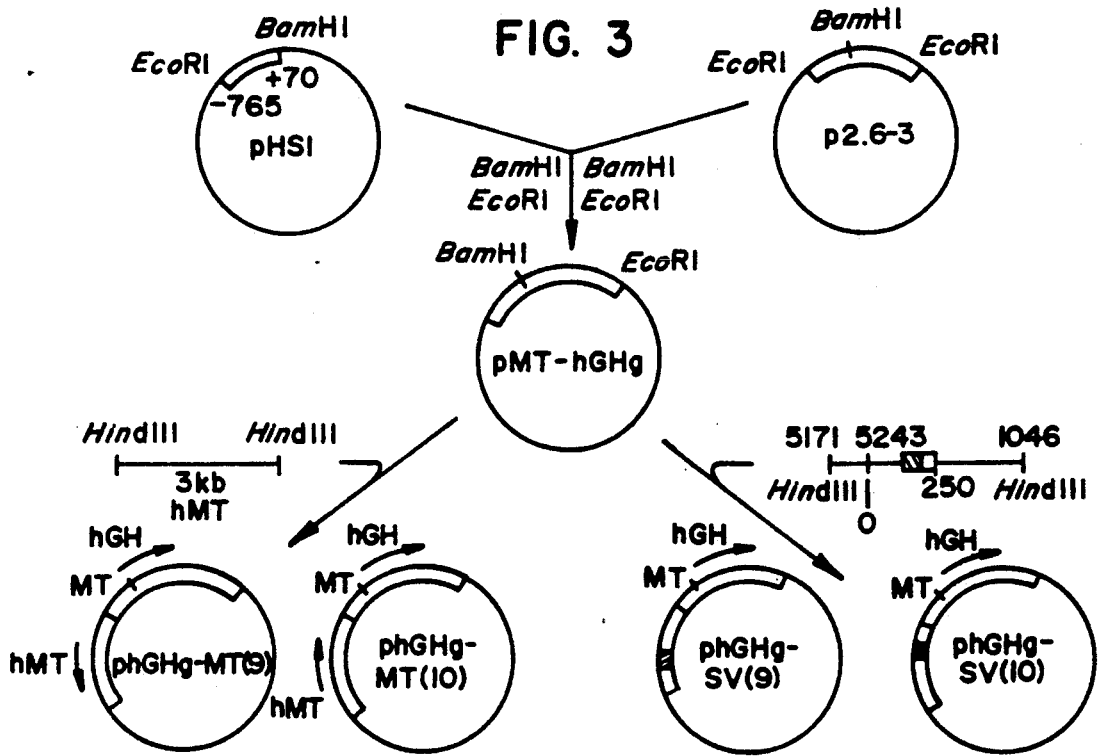
FIG. 3 shows the construction of pMT-hGH, an expression plasmid for human growth hormone, and of the corresponding expression vectors which contain the expressible metallothionein gene (phGH-MT) and the SV40 enhancer (phGH-SV40).

Expression vectors which contain the entire hMT gene useful for selection and amplification were obtained by digesting the pMT-hGHg vectors prepared above with HindIII, treating with alkaline phosphatase, and inserting the 3 kb HindIII fragment containing the hMT gene, in a manner analogous to that used in the construction of pHS1-MT. Again, two orientations, both of them operable, result. This construction is also shown in FIG. 3.

D.3.b. Vectors for Expression of Alveolar Surfactant Protein (ASP)

pMT-ASPc

For the cDNA-containing vector pMT-ASPc, the coding sequences were obtained from the phage vector λ:gHS-15, deposited with ATCC on 7 Dec. 1984 and given accession no. ATCC 40146. The origins of λ:gHS-15 are described in co-pending U.S. Ser. No. 680,358, filed 11 Dec. 1984 now U.S. Pat. No. 4,659,805, assigned to the same assignee and incorporated herein by reference.

The entire ASP coding sequence is excisable from λ:gHS-15 by digestion with BamHI as two fragments, 1.2 kb and 3.5 kb, respectively. pHS-1 was cleaved with BamHI, and the two foregoing BamHI fragments from λ:gHS-15 were ligated into the site. The ligation mixture was transformed into *E. coli* MC1061 to Amp®, and successful transformants screened by restriction analysis. The strain containing the desired construction with the coding sequence of ASP under the control of the hMT-II promoter was designated pMT-ASPc, and propagated to prepare quantities of plasmid DNA.

pMT-ASPg

For the genomic DNA-containing vector, pMT-ASPg, the coding sequences were obtained as an HinfI/EcoRI fragment of the gene extending from nucleotide 950 to nucleotide 3432, containing exons 2, 3, and 4, and part of exon 5 (White, R. T., et al, *Nature* (1985) 317:361-363). This fragment was ligated to a 500 bp fragment from the 3' end of the human ApoAI gene (Shoulders, C. C., *Nucleic Acids Res* (1983) 11:2827-2837) which contains the polyadenylation signal and polyadenylation site. This construction is also described in U.S. Ser. No. 680,358 now U.S. Pat. No. 4,659,805. The entire ASP-encoding genomic insert is shown ligated to the MT-II promoter in FIG. 4.

It was expected that this vector would produce a protein 23 amino acids longer than the native preprotein (which includes the signal sequence). The construct lacks exon 1 and therefore translation probably initiates at the ATG beginning at nucleotide 987 of the genomic sequence complementary to native preprotein mRNA, which nucleotide normally resides in the first intron. In the production of native preprotein, exon 1 is spliced to exon 2 at nucleotide 1022, deleting this start codon, and permitting translation to initiate at nucleotide 1046. However, the additional residues do not appear to interfere with secretion, and the normal mature protein is secreted from cells expressing this modified form of the gene.

pASPc-SV(10)

The coding sequences for ASP were inserted into a modified form of the host vector pHS1-SV(10) which contains the enhancer elements proximal to the MT-II promoter region. First, the 500 bp apoAI fragment was inserted into pHS1-SV(10) by isolating this fragment, obtained by digestion of pMT-Apo (described in Ser. No. 680,358 (supra) and ligating the isolate into EcoRI/BamHI digested pHS1-SV(10). The modified vector was digested with BamHI, blunted, and ligated to the cDNA sequences obtained from pHS10-5 (White, R. T., et al, *Nature* (1985) 317:361-363) as a blunted EcoRI digest. The cDNA fragment extends from the EcoRI linker joined to the 5' untranslated region to the naturally occurring EcoRI site in the 3' untranslated region (900 bp). The relevant nucleotide sequences are shown in FIG. 5, where the starred amino acids represent differences in the primary amino acid sequence from that of the protein obtained from pMT-ASPg. (The differences result from base changes between human cDNA and the genomic sequences.) Initiation of translation is at nucleotide 56, as in the native sequence.

pASPcg-SV(10)

An additional modification was prepared by integrating pASPc-SV(10) and pMT-ASPg sequences. Plasmid pASPc-SV(10) was digested with BamHI and EcoRI, and the isolated larger fragment ligated to the 3' portion of the ASP gene obtained by BamHI/EcoRI (partial) digestion of pMT-ASPg. This represents the portion of the human ASP gene beginning at nucleotide 1154 and extending to nucleotide 3432, this being ligated to the ApoAI gene fragment as above. This construct results in a protein identical to that obtained from pMT-ASPg, but different at amino acid positions 25, 30, and 34 from that obtained from pASPc-SV(10). The nucleotide sequence of the relevant insert is shown in FIG. 6.

D.3.c. Vectors for Expression of Apolipoproteins pMT-AIg and pMT-AIIc

The apolipoprotein AI (apoAI) gene was isolated as a PstI fragment from pSA1.2 followed by polyacrylamide gel purification. This fragment extends from the 5' untranslated region through the entire coding sequence including introns and terminates beyond the polyA addition site. The PstI insert was blunted by treating with T4 DNA polymerase in the presence of dCTP, ligated into SmaI-digested, BAPped pHS1, and the ligation mixture transformed into *E. coli* 1061 to Amp®. The correct construction of the resulting vector, pMT-AIg, was confirmed by restriction enzyme digestion analysis.

In a similar manner, a cDNA sequence encoding human apoAII was cloned into EcoRI-digested pHS1 to obtain an expression vector for apoAII designated pMT-AIIc. The EcoRI insert encoding apoAII was obtained from a human fetal liver cDNA library in λgt10 prepared as described by Huynh, V. T., et al, *DNA Cloning Techniques: A Practical Approach* (IRL Press, Oxford, 1984), which had been probed with a 45 bp oligonucleotide encoding amino acid residues 140-164 of human apoAII (Sharpe, C. R., et al, *Nucleic Acids Res* (1984) 12:3917-3932). Of 750,000 recombinants, 10 positive colonies were obtained, and one of these, designated λAII, had a 440 base EcoRI insert corresponding to the full sequence apoAII cDNA, plus about 20 bases 5' of the untranslated region. This EcoRI insert was used for insertion into pHS1 to obtain pMT-AII.

pAIg-SV40

Expression vectors containing the SV40 enhancer in both orientations operably linked to the genomic sequences encoding apoAI were constructed using SmaI-digested, alkaline phosphatase-treated pHS1-SV(9) and pHS1-SV(10) and inserting a 2.2 kb PstI fragment containing most of the apoAI gene obtained as a PstI digest of pPSA1.3 (described by Seilhamer et al, *DNA* (1984) 3:309; and by Protter, A., et al, *DNA* (1984) 3:449). The 2.2 PstI fragment obtained from the digest was isolated and blunted using Klenow for insertion into the SmaI-cleaved host vectors. The resulting ligation mixtures were transformed into *E. coli* to Amp ® and the correct constructions of pAIg-SV(9) and pAIg-SV(10) were confirmed.

D.3.d. Vectors for Expression of Atrial Natriuretic Factor (ANF)

Atrial natriuretic factor is a protein which regulates the excretion of sodium by the kidneys, and thus controls one of the factors responsible for maintaining proper fluid balance. It is produced in heart atrial cells as a preproprotein and then secreted and processed.

For insertion of the genomic sequence encoding human prepro-ANF, pHS1 was first modified by inserting into the BamHI site, a 24 base BamHI linker fragment isolated from M13mp7, containing convenient restriction sites, including an AccI site. The modified pHS1, designated pHS1', thereby contains this convenient AccI site helpful in the insertion of the ANF coding sequences.

The desired expression vector, designated pMT'-ANF, was constructed by treating pHS1' with AccI and EcoRI, and then with alkaline phosphatase, and inserting a 2016 bp AcyI (partial, blunted)/EcoRI fragment purified from pHGRB-1. This insert contains the entire ANF gene. The relevant DNA sequence is shown in FIG. 7.

D.3.e. Vectors for Expression of Erythropoietin

The gene sequence encoding erythropoietin (Epo) was prepared as follows: The human genomic library, as prepared by Lawn, R. M., et al,*Cell* (1978) 15:1157-1174 in λ-Charon 4A, was probed with the two 24-mers: 5'-TCTGTCCCCTGTCCTGCAGGCCTC-3' and 5'-CTGGGCTCCCAGAGCCCGAAGCAG-3' designed to be complementary to the exons of the Epo gene (according to Jacobs, et al, *Nature* (1985) 313:806-810). A hybridizing phage containing a 15 kb insert was thus obtained, and digested with BamHI and EcoRI to obtain a 4.8 kb fragment which contained the entire coding region of the Epo gene, in addition to 200 bp of the 5' untranslated region and the entire 3' untranslated region. This fragment was isolated on polyacrylamide gel, blunt ended, and ligated into the SmaI site of SmaI-digested, CIP-treated, pUC9 for amplification. The BamHI/EcoRI insert from this cloning vector was then isolated and used to supply the Epo coding sequences in the following vectors:

pMT-Epo pMT-Epo was prepared by cleaving pHS1with BamHI and EcoRI and inserting the Epo coding sequences as a BamHI/EcoRI fragment above.

pEpo-SV(10)

In a similar manner, pHS1-SV(10) was digested with BamHI and EcoRI and the Epo-encoding fragment inserted to provide the SV40 enhancer in proximal operable linkage to the MT promoter.

pEpo-MT

Similarly, but substituting for pHS1-SV(10), pHS1-MT, the desired vector pEpo-MT containing the entire metallothionein gene as an amplification regulator was obtained.

pEpo'-SV(10)

pEpo-SV(10) was modified to provide, insofar as permitted by the desired coding sequence, a gene having a Kozak concensus sequence at the 5' end and a polyadenylation site at the 3' end. The Epo gene described above lacks the polyadenylation site known to be required for efficient translation.

pEpo-SV(10) was digested with ScaI which cuts 7 bases following exon I in the first intron. The resulting blunt ended site was ligated to the oligomer

```
5'-GATCCAAGATGGGGGTGCACGGT-
    GAGT-3'GTTCTACCCCCACGTG-
    CCACTCA
``` to replace the missing portions of the gene N-terminus, to provide the concensus sequence, and to provide a BamHI site at the upstream end. The ligation mixture was treated with BamHI (which removes the 5' untranslated regions of the gene from the end of the vector), and religated to obtain an intermediate vector containing the Epo gene with a modified 5' terminus.

Figure 8:
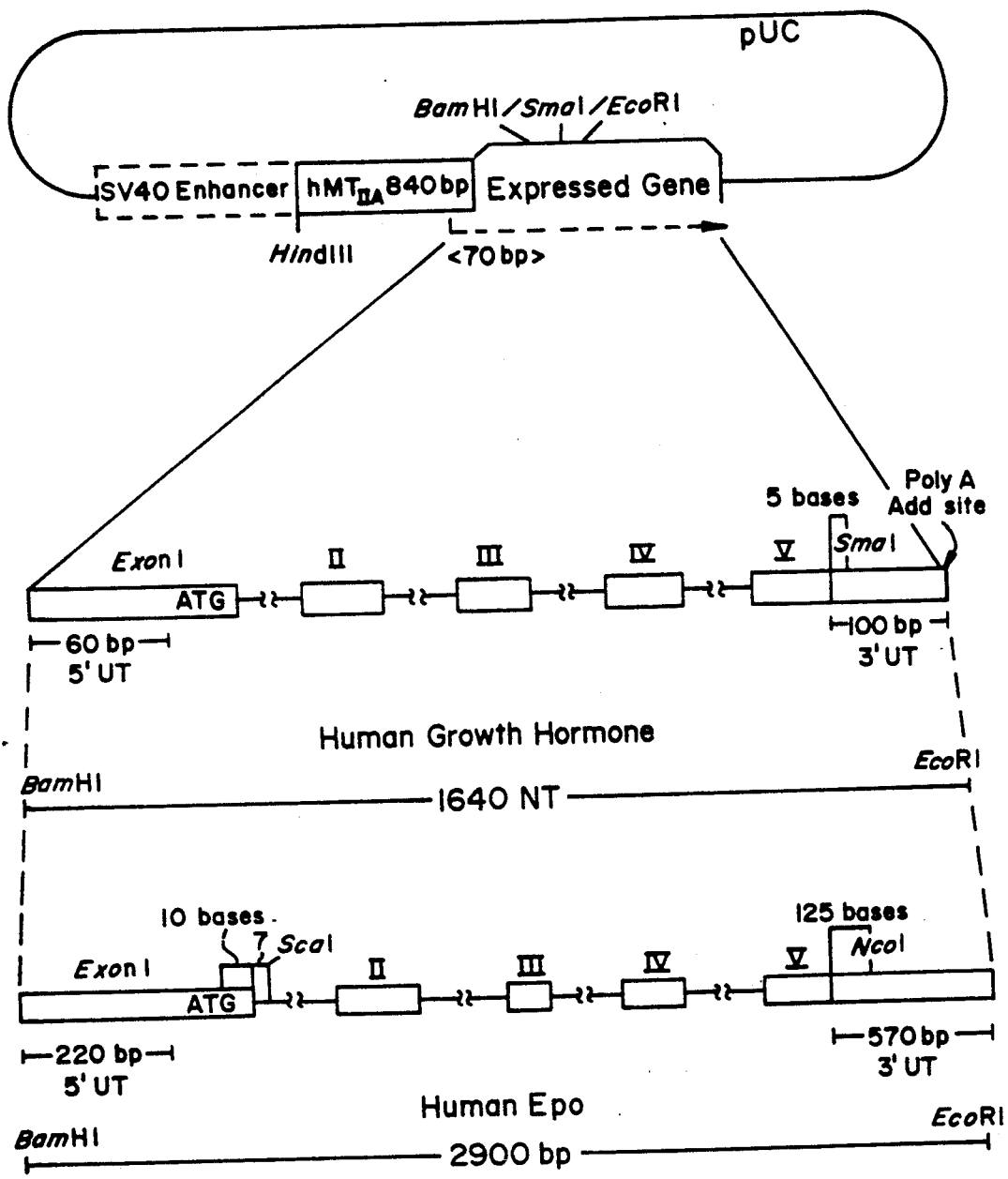
FIG. 8 shows the construction of the modified Epo gene.

For the 3' end modification, phGHg-SV(10) was digested with BamHI and SmaI and treated with CIP to provide a host vector lacking the coding sequences for hGH. This linearized vector was ligated to a BamHI/NcoI fragment from the intermediate vector prepared above containing the 5' modified Epo gene lacking most of the 3' untranslated region to provide pEpo'-SV(10) which contains the desired modified gene. The construction is outlined in FIG. 8.

D.4. Generation of Mammalian Transformants

Each of the vectors described above was transformed into CHO cells as follows: Chinese hamster ovary (CHO)-K1 cells were grown on medium composed of a 1:1 mixture of Coon's F12 medium and DME21 medium with 10% fetal calf serum. The cells were co-transformed with the vector of interest and pSV2:NEO (Southern, P., et al, *J Mol Appl Genet* (1982) 1:327-341). pSV2:NEO contains a functional gene conferring resistance to the neomycin analog G418. In a typical transformation, 1.5 μg of pSV2-NEO and 15 μg or more of the expression vector DNA are applied to a 100 mm dish of cells. The calcium phosphate-DNA co-precipitation according to the protocol of Wigler, M., et al, *Cell* (1979) 16:777-785, was used with the inclusion of a two minute "shock" with 15% glycerol in PBS after four hours of exposure to the DNA.

Briefly, the cells are seeded at 1/15 confluence, grown overnight, washed 2×with PBS, and placed in 0.5 ml Hepes-buffered saline containing the Ca-PO$_4$.DNA co-precipitate for 15 min and then fed with 10 ml medium. The medium is removed by aspiration and replaced with 15% glycerol in PBS for 1.5-3 min. The shocked cells are washed and fed with culture medium. Until induction of MT-II-controlled expression, the medium contains F12/DMEM21 1:1 with 10% FBS. A day later, the cells are subjected to 1 mg/ml G418 to provide a pool of G418-resistant colonies. Successful transformants, also having a stable inheritance of the desired plasmid, are then plated at low density for purification of clonal isolates.

D.5. Assay for Production Levels of Desired Protein

The transformants are assayed for production of the desired protein, first as pools, and then as isolated clones in multi-well plates. The plate assay levels are somewhat dependent on the well size—e.g. results from 24 well plates are not directly comparable with those from 96 well plates. Clones which are found by plate assay to be producing the protein at a satisfactory level can then be grown in production runs in roller bottles. Typically, the levels of production are higher when the scale up is done. However, there is not an absolute correlation between performance in the plate assay and in roller bottles—i.e. cultures which are the best producers in the plate assay are not necessarily the best after scale-up. For this reason, typically 100-200 or more individual clones are assayed by various screening methods on plates and 5-10 of the highest producers are assayed under production conditions (roller bottle).

D.5.a. Production of hGH

Plate Assays

Small amounts of the isolates from cells transformed with the hGH-encoding plasmids were grown in multi-well plates after exposure to $10^{-4}$M zinc chloride for convenient assay of growth hormone production. Growth hormone determinations were made by standard radioimmunoassays using commercially available reagents (Hybritech, Inc.). Two of 60 clonal isolates from pMT-hGH transformants (CBI-25 and CBI-37) produced large amounts of the desired hGH. CBI-37 was deposited with the ATCC on 7 Feb. 1985 and given Accession No. CRL-8721.

For cells transformed with phGH-MT(9) or phGH-MT(10), additional steps for cadmium resistance selection were employed to select appropriate transformants. A pool of G418-resistant cells were seeded at 1/10 confluence and grown in the presence of $5\times10^{-5}$M zinc chloride and various amounts of cadmium chloride. A similar pool of transformants carrying pMT-hGH were used as controls. No surviving colonies were obtained at concentrations as low as 2.5 $\mu$M $Cd^{+2}$ when the pMT-hGH pool was used for seeding. However, more than 500 colonies survived in media seeded with phGH-MT transformants at 2.5 $\mu$M $Cd^{+2}$, about 100 colonies at 5 $\mu$M $Cd^{+2}$, and 2 colonies at 10 $\mu$M $Cd^{+2}$. No colonies survived at 20 or 50 $\mu$M $Cd^{+2}$. The 10 $\mu$M $Cd^{+2}$ resistant colonies were discarded because of abnormal morphology, but colonies from the 2.5 $\mu$M and 5 $\mu$M $Cd^{+2}$ were grown to confluence to create new pools for comparison of hGH production levels with transformants that were not selected for resistance to cadmium.

Pools of transformants were induced for hGH production to obtain comparisons of production levels with and without enhancers or $Cd^{+2}$ selection. The cells were seeded into 10% serum with G418 at 10% confluence. Three days later when the cells are confluent, the cells were washed with PBS and refed with serum-free medium containing $3\times10^{-5}$M $FeSO_4$ and $7\times10^{-5}$M $Zn^{+2}$.

Figure 9:
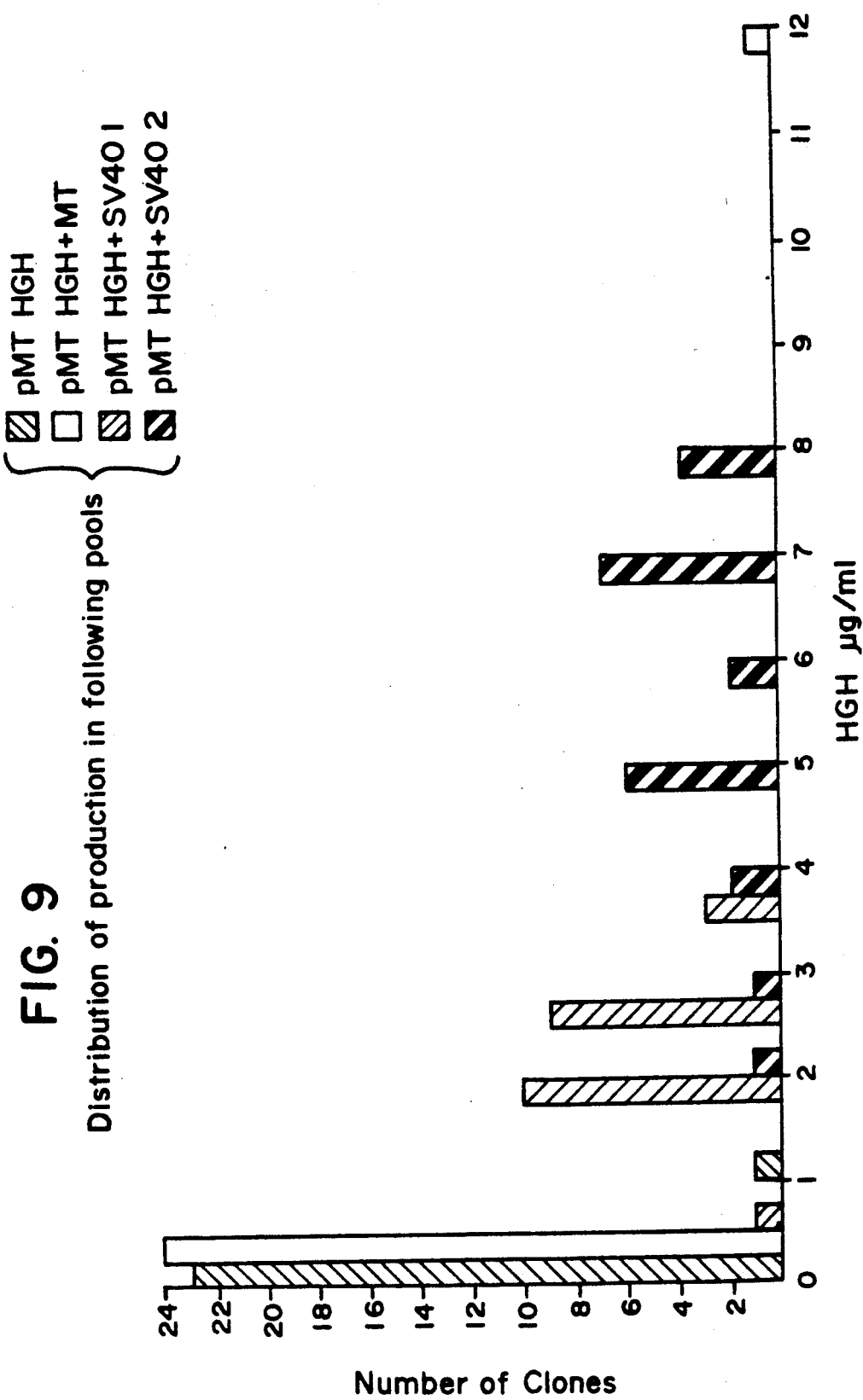
FIG. 9 shows the distribution of hGH production capability of the various colonies derived from pools of CHO cells transformed with pMT-hGH, phGH-MT, and phGH-SV40.

Transformants with pMT-hGHg showed production levels of 1.4 $\mu$g/ml, as did clones transformed with phGHg-MT not selected for cadmium ion resistance. However, phGHg-MT transformants selected in 2.5 $\mu$M or 5 $\mu$M $Cd^{+2}$ produced 6.5 and 17.5 $\mu$g hGH/ml, respectively. Cells transformed with phGHg-SV(9) or phGHg-SV(10), respectively, produced 7.0 $\mu$g/ml and 17.0 $\mu$g/ml hGH. FIG. 9 shows a graphic representation of the distribution of hGH production levels for individual clones in the various pools. It is clear that phGHg-SV40 transformants exhibit superior properties to transformants with pMT-hGHg or with phGHg-MT in the absence of cadmium ion. The construction wherein the enhancer element is closer to the transcription start appears to give higher yields.

Clones were isolated from the pool resistant to 5 $\mu$M cadmium ion and three of the best colonies were isolated. Cd-5-4, Cd-5-12, and Cd-5-15 when grown under production conditions (see below) yielded as high as 120 $\mu$g/ml of hGH. When assayed under plate assay conditions, Cd-5-12 yielded 21.5 $\mu$g/ml and Cd-5-15 yielded 29.0 $\mu$g/ml hGH; other clones, less successful under production conditions, yielded 50-70 $\mu$g/ml. Southern blots confirmed that cells picked for 5 $\mu$M cadmium ion resistance contained about 20 copies of the expression vector, while the pool which was not cadmium-selected contained an average of 1-3 copies.

An additional set of transformants was obtained by treating the cells with a DNA mixture containing $\pm 1.5$ $\mu$g pSV2-Neo, 15 $\mu$g phGHg-SV(10) and 10 $\mu$g pUC9/MT to obtain the results simultaneously taking advantage of cadmium selection and the enhancer activity of the SV40 segment. A neo-resistant pool was obtained and subsequently subjected to selection in 20 $\mu$M cadmium ion and 10 individual clones picked and grown in a 96 well dish. The best of these 10 clones produced hGH at 155 $\mu$g/ml.

Production Runs

Standard Induction

The CBI-25 and CBI-37 cells, which had been shown to produce hGH under suitable conditions, were seeded into roller bottles at 1/10 confluence in basal medium supplemented with 10% fetal calf serum, incubated overnight, and then induced for growth hormone production by addition of zinc chloride in the concentration range of $1\times10^{-4}$M to $3\times10^{-4}$M. hGH levels rise for 7-10 days, with a final accumulated concentration of 35 mg/l under optimal inducing conditions, $2\times10^{-4}$M $ZnCl_2$ (see FIG. 1).

Figure 10:
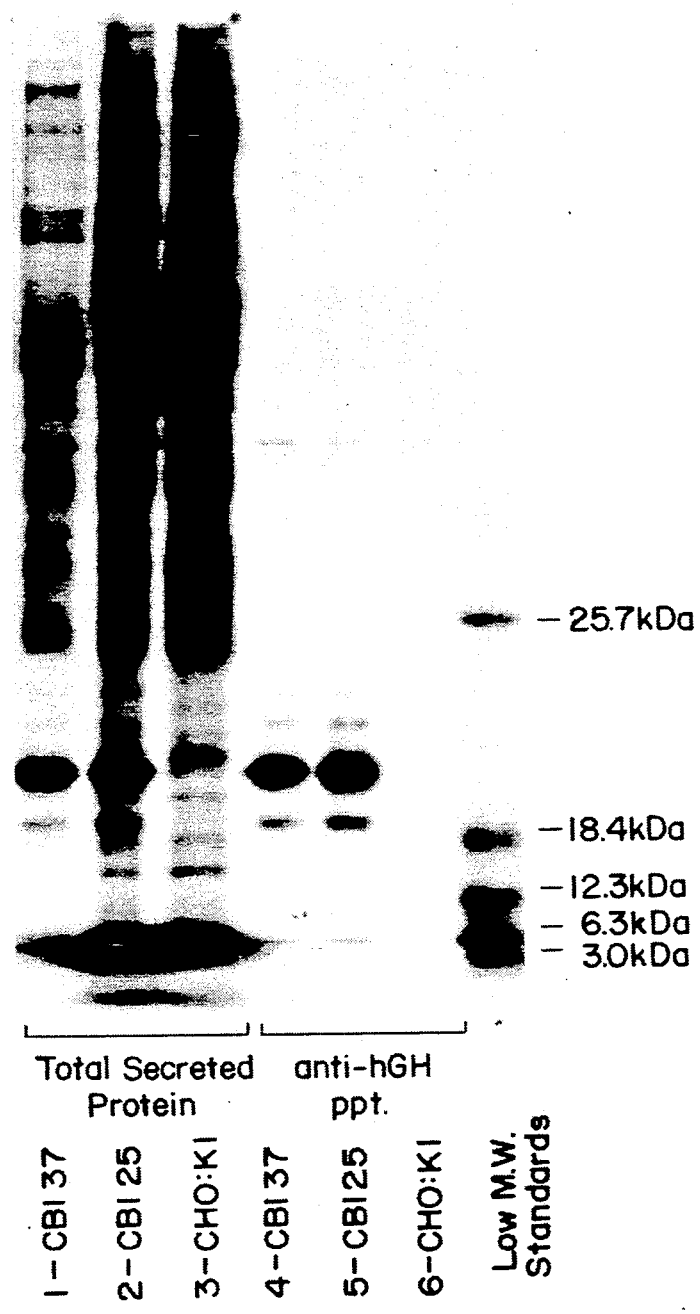
FIG. 10 shows the results of polyacrylamide gel electrophoresis on radiolabeled proteins secreted by CBI-25 and CBI-37.

FIG. 10 shows the behavior on gels for $^{35}$S-methionine labeled proteins secreted by CBI-25 and CBI-37. After six hours of incubation with $1\times10^{-4}$M zinc chloride, $^{35}$S-methionine was added to the culture, and the proteins secreted into the medium were analyzed by electrophoresis on 15% SDS-acrylamide gels, followed by autoradiography. In FIG. 9, lanes 1, 2 and 3 show total secreted proteins from, in order, CBI-37, CBI-25, and untransformed CHO-K1 cells. The media from the transformed cells show the presence of a major band at approximately 22 kD not present in the untransformed cells. Lanes 4, 5, and 6 show corresponding results for proteins immunoprecipitated with rabbit antiserum to hGH. It is particularly clear from the results in the immunoprecipitate that two major protein bands, corresponding to 22 kD and 20 kD are present. The proportion of the 20 kD band is roughly 10% of the total, corresponding to the second (20 kD) species variant found in growth hormone produced by the human pituitary.

Prolonged exposure of the autoradiograph also shows two minor related species of higher molecular weight, consistent with pregrowth hormone and pre-20 kD growth hormone. The identity of the 22 kD species as mature hGH was further confirmed by comparison with pituitary hGH in reduced and unreduced gel electrophoresis, and by ability to compete with radio labeled hGH for growth receptors on IM9 human lymphocytes (Rosenfeld, R. G., et al, *Biochem Biophys Res Comm* (1982) 106:202).

Production in Serum-Free Medium

CBI-37 cells were also grown under pilot production conditions and induced in the absence of serum. The cells were seeded into a 490 cm square roller bottle in Coon's F12/DME21, 1/1 medium supplemented with 10% fetal calf serum and 15 mM Hepes. When the cells had reached near confluence (3-4 days), the cells were washed 2× with $Ca^{+2}$ and $Mg^{+2}$ containing PBS, and the medium was replaced with the same basal medium (serum free and including 15 mM Hepes) containing $6-8\times10^{-5}M$ zinc chloride and $3\times10^{-5}M$ iron (II) ion, in place of the fetal calf serum supplement. (It was found that human transferrin at least 5 µg/ml could be substituted for the iron ion.) Growth was continued under these conditions by harvesting the medium 2-3 times weekly, and replenishing it with fresh serum-free medium. The secreted hGH was harvested at the rate of 2.5 mg/day. Proportionately more hGH was obtainable from production bottles 2-4 times this size. Production may be extended indefinitely, and has been continued for as long as 8 weeks.

Figure 11:
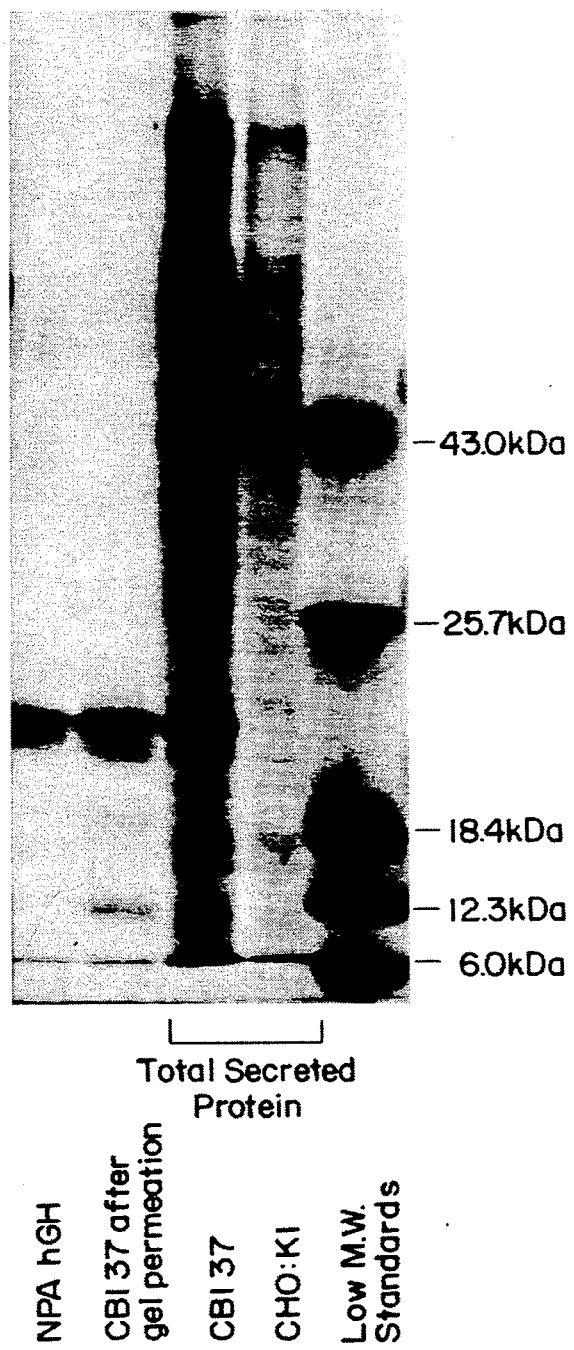
FIG. 11 shows a comparison by SDS-PAGE of pituitary-secreted hGH with hGH preparations from CBI-37 cells.

FIG. 11 shows the results of SDS-PAGE on proteins from the medium obtained above stained with Coomassie blue. The CBI-37 cell medium shows the presence of hGH species not present in the controls, and purification of the medium proteins with the single step of gel permeation column results in hGH which is approximately 90% pure, as there shown.

Additional similar production runs utilizing a cadmium-resistant transformant containing phGHg-MT (Cd-5-15) and a transformant containing phGHg-SV(10) (V-18) were made for purposes of comparison. Typical results are tabulated in Table 1 below. Day zero is counted when preinduction medium is discarded and the cells are refed with medium containing $6-8\times10^5M$ zinc ion, $3\times10^{-5}M$ iron (II) and 15 mM Hepes.

TABLE 1

| Day | hGH (µg/ml) | | | Accumulated hGH (mg/roller)* | | |
|---|---|---|---|---|---|---|
| | CBI-37 | Cd-5-15 | V-18 | CBI-37 | Cd-5-15 | V-18 |
| 0 | — | — | — | — | — | — |
| 2 | | 94.5 | 21 | | 11.8 | 2.6 |
| | 28.6 | | | 3.6 | | |
| 4 | | 89.5 | 38 | | 23 | 7.4 |
| | | | 32 | | | 11.4 |
| 6 | | 83.5 | 36 | | 33.4 | 15.9 |
| | 32.2 | 56.0 | 47 | 7.6 | 40.4 | 21.7 |
| 8 | | | 56 | | | 28.7 |
| | 33.0 | | 53 | 11.7 | | 35.4 |
| 10 | | 58.5 | 42 | | 47.1 | 40.6 |
| | 40.3 | | 32 | 16.7 | | 44.6 |
| 12 | | | 39 | | | 49.5 |
| 14 | 31.6 | 40.5 | | 22.6 | 52.2 | |
| 16 | 33.3 | | | 26.8 | | |
| 18 | 35.6 | | | 31.4 | | |
| 20 | 30.4 | | | 37.5 | | |

*Each roller bottle contains 250 ml medium.

As shown above, the average hGH accumulated per day in the roller bottle is 1.9 mg/day (7.6 µg/ml/day) for CBI-37, 4.4 mg/day (17.6 µg/ml/day) for Cd-5-15, and 4.1 mg/day (16.4 µg/ml/day) for V-18.

D.5.b. Alveolar Surfactant Protein

Plate Assays

Pools of cells transformed with the various ASP encoding plasmids were grown in multi-well plates and then exposed to $5\times10^{-5}$ to $1\times10^{-4}$ zinc ion concentration to induce production of ASP. ASP assays were conducted using Western blot employing immunoprecipation with rabbit anti-human ASP polyclonal antiserum followed by $^{125}I$ protein A and autoradiography.

In more detail, semiconfluent monolayers of individual cell lines growing in McCoy's 5A medium with 10% FBS were washed with phosphate-buffered saline (PBS) and refed with McCoy's containing 10% FBS, $1\times10^{-4}$ zinc chloride, and 0.25 mM sodium ascorbate. (Ascorbate may be helpful in mediating the hydroxylation of proline residues.) Twenty-four hours post induction, the cells were washed with PBS and refed with serum-free McCoy's containing the zinc chloride and ascorbate. After 12 hours, the conditioned media were harvested, made 20 mM in Tris, pH 8, and filtered through nitrocellulose in a BRL dot-blot apparatus. The nitrocellulose filter was blocked in 50 mM Tris, pH 7.5, 150 mM NaCl (Tris/salt) containing 5% nonfat dry milk, and then incubated with 1:5000 dilution of rabbit anti-human ASP polyclonal antiserum in the blocking solution, washed several times in the above Tris/salt, and incubated with 25 µCi of $^{125}I$ protein A in blocking solution, washed, and autoradiographed.

Most pools transformed with the ASP encoding vectors did not produce ASP detectable in this assay. However, a positive, ASP-secreting cell line, designated A-38, was selected from pMT-ASPg transformants. In addition, certain pools from cells transformed with pASPc-SV(10), designated ASP-I, or with pASPcg-SV(10), designated ASP-F and ASP-G, produced levels of ASP comparable to those produced by the cell line designated D-4 described below (~2-5 µg/ml).

Characterization of ASP Protein

The A-38 cells (supra) were grown to 25% confluence in McCoy's 5A medium containing 10% FBS and then induced with $10^{-4}M$ zinc chloride in McCoy's containing 10% FBS and 0.25 mM sodium ascorbate. (Half of the cells were also treated with $10^{-6}M$ dexamethasone.) Twenty-four hours later, the cells were washed with PBS and refed with RPMI medium containing 10% dialyzed FBS, $1\times10^{-4}M$ zinc chloride, 0.25 mM sodium ascorbate, and 0.5 mCi/ml $^{35}S$-methionine.

Figure 12:
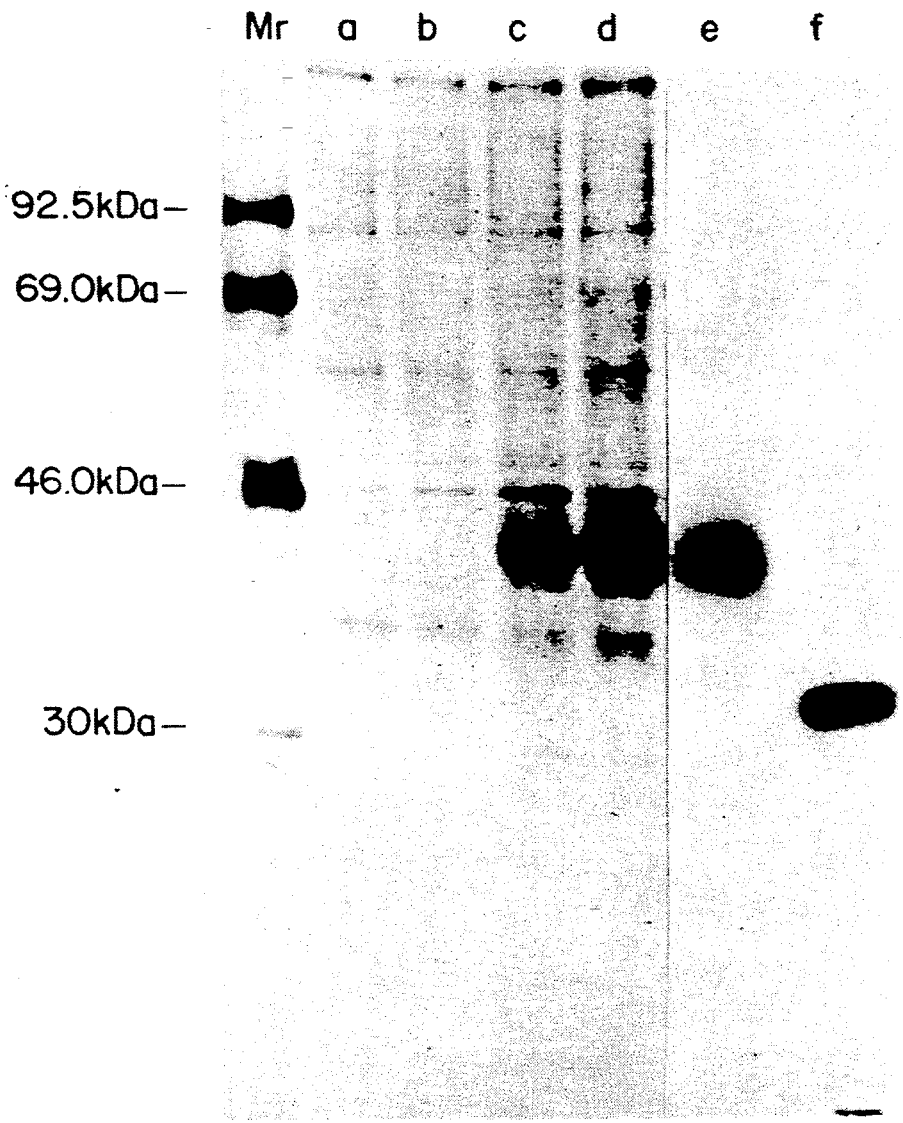
FIG. 12 shows SDS-gel results for Endo-F treated and untreated supernatants from ASP-producing transformant A-38.

Eighteen hours later, the cell supernatant was made 1 mM phenylmethylsulfonylfluoride and immunoprecipitated with rabbit anti-canine ASP antiserum using protein A as carrier. Half of the precipitated protein was boiled in SDS-PAGE sample buffer, and the other half eluted into 0.75% Triton X-100, 0.075% SDS, 0.75% 2-mercaptoethanol, 30 mM EDTA, 75 mM sodium phosphate, pH 1 and incubated for 1 hr at 37° with 0.5 units of endoglycosidase-F (endo-F). Endo-F treated and untreated protein fractions were subjected to SDS-PAGE with the results shown in FIG. 12. The Endo-F treated fraction showed a 30 kD protein (lane F) as compared to 38 kD protein for the untreated (lane E). (Lane M contains size markers, lanes A and B supernatants from untransformed CHO cells, and lanes C and D supernatants from A-38 cells untreated and treated with dexamethasone, respectively.)

Supertransfection to Prepare D-4

An additional cell line, designated D-4, was obtained by supertransfection of A-38 with a mixture of pMT-ASPg (20 µg) and pSV2:GPT (1 µg). Semiconfluent monolayers of A-38 growing in F12/DMEM21 with 10% FBS were co-transfected, as described above.

After 48 hours the cells were split 1:5 into F12/DMEM21 containing 10% FBS and HAT selection drugs. After 17 days of HAT selection, the pool of surviving resistant clones was screened for individual clones producing high levels of ASP by the immunofilter screen method of McCracken, A. A., et al *Biotechniques* (March/April 1984) 82-87. Briefly, the cells were seeded onto plates at 100 cells per 100 mm dish in F12/DMEM21, 10% FBS. After 5 days (when colonies contain 50-200 cells each), the cells were washed with PBS, refed with serum-free F12/DMEM21, and overlayed with a sterile teflon mesh. On top of the mesh was placed a nitrocellulose filter which was left in place for 8 hr. The nitrocellulose was removed and treated as an immunoblot, first with rabbit anti-canine ASP polyclonal antiserum, then $^{125}$I protein A, followed by autoradiography. Of approximately 2000 colonies screened, two gave a detectable signal and one, designated D-4, was shown to express the ASP gene at 10-20 times the level of A-38, or at an amount corresponding to an estimated 2-5 μg/ml ASP.

Characterization

The secreted ASP from the D-4 cell line was isolated from the serum-free medium by affinity chromatography and sequenced at the N-terminus on a gas-phase microsequencer. Determination of a 16 amino acid sequence showed complete homology with the N-terminal portion of the protein isolated from lung lavage; 70% of the total contained an N-terminal Glu residue; the remaining 30% was clipped so as to contain an N-terminal Val (position 2 relative to Glu). This is the same composition as the isolated lavage protein. Hydroxyprolines were present at positions 10, 13, and 16, indicating the ability of the cells to exhibit post-translational processing.

Figure 13:
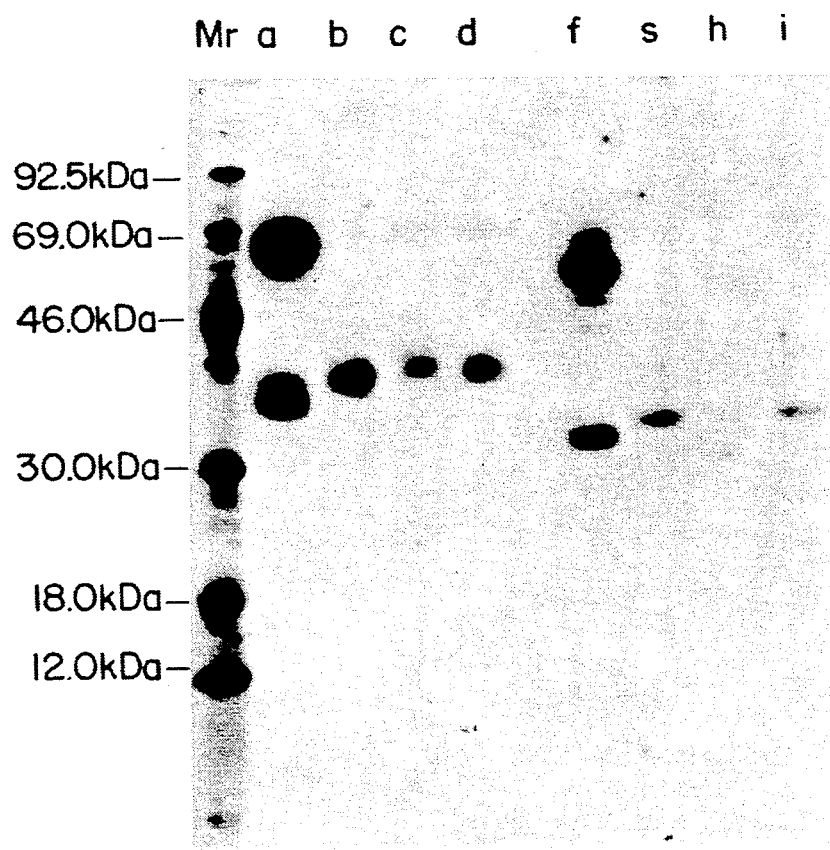
FIG. 13 shows SDS-gel results for Endo-F treated and untreated supernatants from ASP-producing transformant D-4.

In addition, the protein secreted by D-4 along with the secreted protein fraction from pool ASP-I (supra) and from pool ASP-G (supra) was compared to human proteinosis lung lavage protein using Western blot. Serum-free medium from induced cells was TCA precipitated, treated (or not) with Endo-F and subjected to SDS-PAGE in 12.5% gels. The gel was electroblotted and dot-incubated with rabbit antihuman ASP polyclonal antiserum followed by $^{125}$I protein A. The results are shown in FIG. 13.

Lanes A and F contain 1 μg alveolar proteinosis protein before and after Endo-F digestion; lanes B, C, and D represent media from D-4, ASP-I pool, and ASP-G pool respectively untreated with Endo-F; lanes G, H, and I represent proteins from these supernatants treated with Endo-F. It is evident that Endo-F treatment reduces the apparent molecular weight of all proteins, and results in more discrete bands.

Production Runs

The supertransfected cell line containing multiple copies of pMT-ASPg (cell line D-4) was used in a production level run in roller bottles. An 850-cm square roller bottle was seeded with a 10 cm dish containing $2 \times 10^6$ cells in 10% FCS, 15 mM Hepes, pen-strep, and glutamine. After the cells reached confluence (2-3 days), they were washed 2× with PBS and replaced with 250 ml of F12/DMEM21, 10 mM Hepes without FCS. The following day the cells were refed with 250 ml of F12/DMEM21, 10 mM Hepes, $5 \times 10^{-5}$ zinc chloride, $10^{-6}$M dexamethasone, and 0.25 mM ascorbate. The cells were harvested every 2 days, spun for ten minutes at 1000 rpm, and frozen at $-20°$ C. Production was 1-5 μg/ml/day, assayed by dot-blot Western using polyclonal anti-canine ASP antisera at 1:5000 dilution, as described above. Production drops after about 14-17 days.

D.5.c. Apolipoproteins

Plate Assays

Cells transformed with apolipoprotein expression vectors were verified for production of apolipoprotein by detecting a protein of the correct molecular weight when the cells were permitted to incorporate a $^{35}$S methionine.

Transformants, with either pHS1' (as a control) or pMT-AI, were grown to 70% confluence in 9.6-cm square wells in standard medium (RPMI plus 10% dialyzed FBS). The cells were preinduced with $1.5 \times 10^{-4}$M zinc chloride for 7 hr, at which time 0.15 μg/ml L-[$^{35}$S] methionine was added. Cells were incubated in the presence of label overnight, and the media harvested. Portions of the media containing $1 \times 10^5$ cpm were added to SDS-gel sample buffer and incubated at 100° C. for 2 min; second portions ($5 \times 10^5$ cpm) were brought to 1 ml final volumes using 50 mM Tris-HCl, pH 6.8, 0.15M NaCl, 0.1 mM EDTA, and 2% (V/V) Triton-X 100. Two μl of rabbit anti-human apoAI was added to the suspension, which was then incubated, reacted with protein A sepharose, and washed.

Pools of cells transformed with pMT-AI, as contrasted with pHS1' transformants, show the expected 25 kd band characteristic of the mature native apoAI when run on gels, which band is specifically immunoreactive against human apoAI.

In a similar manner, CHO cells were transformed with pMT-AII, and the production of apoAII protein verified.

To obtain individual colonies from the AI-producing pool, the cells were plated at low density (100-200 cells/ml) in F12/DMEM21 with 10% FBS to produce individual colonies after 4-7 days at 37° C. The colonies were picked and grown to a cell density of about $10^6$ cells/ml and then individually assayed for apoAI expression by dot blot Western, using the method of Jahn et al, *Proc Natl Acad Sci (U.S.A.)* (1984) 81:1684-1687.

For apoAI production, the individual colonies were seeded at 25% confluence in 12-well dishes in 1.5 ml F12/DMEM21 plus 10% FBS. After 24 hours the cells were washed with 1 ml PBS and fresh medium containing $1 \times 10^{-4}$M zinc sulfate was added to begin preinduction. Sixteen hr later the cells were washed twice with 1 ml PBS and refed with 0.65 ml serum-free medium containing $3 \times 10^{-5}$M zinc sulfate and $3 \times 10^{-5}$M iron (II) sulfate. After 48 hr of serum-free induction, the media were harvested, centrifuged at 1000 rpm for 5 min to remove cell debris, and 0.5 ml of the supernatants applied to a nitrocellulose filter for assay as described by Jahn, et al (supra).

Two high-producing apoAI cell lines, designated Clones 104 and 143 were further verified to produce apoAI incorporating $^{35}$S methionine. ApoAI from both of these cell lines is produced at a 30-fold higher level than the pool cells and is identifiable in total secreted medium proteins without immunoprecipitation. Clone 104 was deposited with the American Type Culture Collection on 3 Oct. 1985 and has ATCC number 8911.

Effect of Enhancer

Pools of transformed cells were selected and screened for apoAI production using cells transformed with pAIg-SV(9) and pAIg-SV(10). Individual colonies were obtained from these pooled as described above and were cultured and induced for the production of apoAI.

For comparison of expression levels with those of controls (pHS1' and pMT-AI) the individual colonies were subjected to analysis for apoAI in the medium as follows: After the 48 hr of serum-free induction and centrifugation to remove cell debris, protein was precipitated from 0.4 ml samples of the media by the addition of TCA to 10%, and addition of 20 µg bovine insulin as carrier protein. Samples were incubated on ice for 30 min followed by centrifugation at 3000 rpm for 30 at 4° C. The pellets were washed once with 0.5 ml ice cold acetone and then solubilized in 40 µl SDS-gel sample buffer and applied to a 10-20% gradient SDS-PAGE gel according to Laemmli (*Nature* (1970) 227:680). The gel was stained with Coomassie blue, giving the results shown in FIG. 14.

Lane 1 represents the pHS1' control; lane 11 represents clone 143; lanes 18 and 19 represent clone 143 grown in roller bottle cultures (which results in higher production); and lane 20 contains molecular weight markers. Lanes 3-10 represent various clones from the pool of pAIg-SV(9) transformants. Lanes 3-17 represent individual colonies from the pool of pAIg-SV(10) transformants. Lanes 2 and 12 represent pools harboring pAIg-SV(9) and pAIg-SV(10), respectively.

Figure 14:
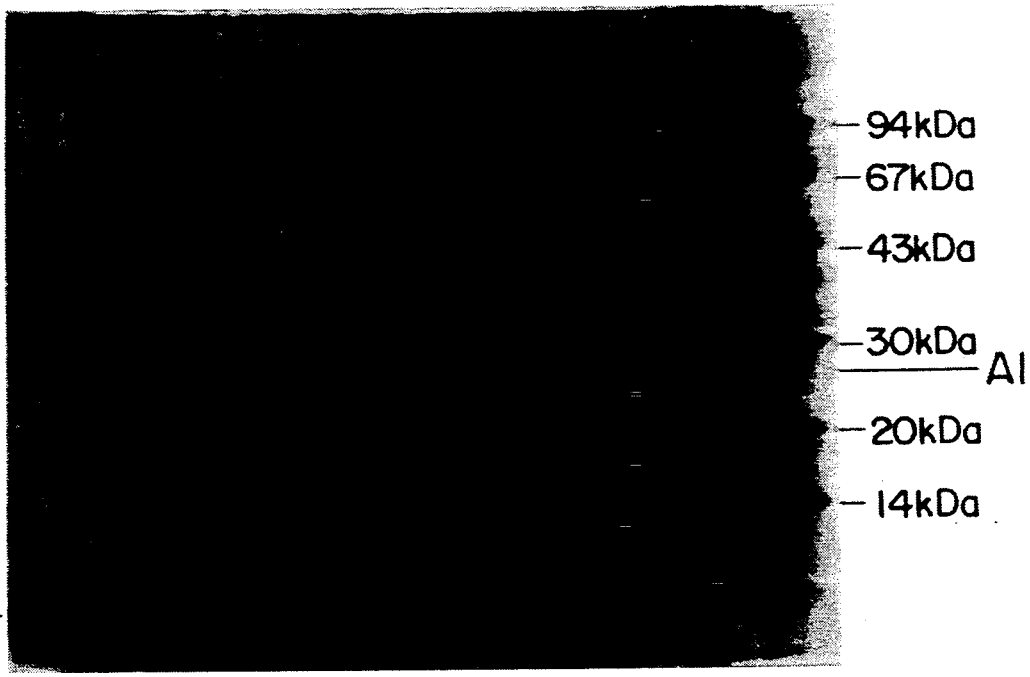
FIG. 14 shows a polyacrylamide gel of extracts from CHO cells transformed with various apolipoprotein AI (ApoAI) expression vectors.

It is apparent from FIG. 14 that most of the individual clones picked from the enhanced pools produce apoAI at levels higher than clone 143, and that the enhanced pools themselves already produce apoAI at levels equal to clone 143. The production levels are estimated to be above 30 µg/ml.

Production Runs

The pMT-AI-transformed cells designated Clone 104 were grown in 850-cm square roller bottles as described for pMT-ASPg above. After 2 days of incubation in the original serum-containing medium at 37° C., zinc sulfate was added to a concentration of $1 \times 10^{-4}$M, and 1 day later the cells were switched to a serum-free F12/DMEM21 medium containing $6 \times 10^{-5}$M zinc sulfate to induce apoAI production. Two days later the cells were refed with the same protein-free medium but containing $7 \times 10^{-5}$M zinc sulfate. This is designated "day zero". After day zero, the medium was assayed periodically for apoAI production by centrifugation of a portion of the medium to separate cell debris followed by fractionation of the medium on SDS-gel electrophoresis and staining with Coomassie blue. The stained gels were scanned to quantitate the amount of apoAI protein using purified apoAI standard obtained from Calbiochem (La Jolla, Calif.). The cells were refed periodically as above. ApoAI expression increased over the first 6 days from about 10 µg/ml/day at day 2 to 20 µg/ml/day at day 5 and then plateaued at about 30 µg/ml/day.

Characterization and Complexation of ApoAI

The culture supernatants from the production runs in the previous paragraph were shown to be correctly processed and to form lipoprotein complexes similar to those found natively.

The ability of the apoAI to complex with endogenous lipid in the CHO cells was shown as follows: The medium conditioned by clone 143 was adjusted to a density of 1.125 g/ml by addition of solid potassium bromide, then centrifuged at 38K rpm for 18 hours in a swinging-bucket rotor. The top fraction was removed by a conventional slicing method, and dialyzed extensively against saline. The material, when examined by SDS gel electrophoresis, gave a prominent band in the 25 kd range, corresponding to apoAI. About 10%-20% of the total apoAI was in the upper fraction, as judged by the relative staining intensities of the 25 kd bands on SDS gels.

Figure 15:
FIG. 15 is an electron micrograph of the complex formed by apoAI from transformants with endogenous lipid.

Electron micrography of the top-fraction material shows the presence of numerous disc-shape structures characteristic serum of apoAI/phospholipid complexes (described in Hamilton, R. L., et al, *J Clin Invest* (1976) 58:667-680), as shown in FIG. 15.

The ability of the apoAI to complex with INTRALIPID (Cutter Labs, Berkeley, Calif.) was shown in an additional protocol. INTRALIPID is an artificial lipid emulsion composed of soybean triacylglycerol and egg lecithins. The mesophase, or phospholipid-rich portion of the emulsion was removed by ultracentrifugal floatation in a discontinuous sucrose gradient. The bottom layer contained 2 ml of emulsion, 0.6 g sucrose and saline to give a final volume of 4 ml and a density of 1.06 g/ml. This layer, in a polyallomer tube of a Beckman SW41 rotor, was overlayed with 6 ml of an NaCl solution of d=1.02 g/ml. Finally a third layer was made of 2 ml of saline solution of d=1.006 g/ml. Centrifugation was at 28,000 rpm at 10° C. for 60 minutes.

After centrifugation, the triglyceride rich emulsion on the top of the gradient was separated from the infranatant solution by the tube slicing technique using a Beckman slicer.

The culture medium was concentrated 100 times by ultrafiltration using an Amicon YM 10 membrane. The concentrated medium was incubated with purified INTRALIPID and centrifuged as described for INTRALIPID above. Lipid-to-protein ratios of either 0.1, 0.3, or 0.6 ml of concentrated medium per ml INTRALIPID were used.

A sample from each top fraction was delipidated, fractionated by SDS-PAGE and the gels stained with Coomassie blue. ApoAI is the only major protein that is separated with the less dense INTRALIPID fraction, and increasing quantities of medium yield increasing amounts of purified apoAI. The purity of apoAI was about 95%, as determined by staining density on the gels. The fraction not treated with INTRALIPID contains some apoAI and other contaminating proteins secreted from the CHO cells.

The apoAI from the production run above was further purified for additional complexation studies as follows: The apoAI enriched, delipidated protein precipitate was dissolved in 0.01M Tris-HCl, pH 8.3, buffer made in 6M urea. A 50 µl aliquot was injected in a high-performance liquid chromatography system (HPLC) with a $C_{18}$ column equilibrated in a 20% acetonitrile, 0.1% trifluoroacetic acid (TFA) solution. After injection the sample was eluted with a gradient of acetonitrile from 20% to 70% containing 0.1% TFA at 2 ml/min flow rate to obtain a single major peak. The fractions corresponding to this peak were pooled and acetonitrile was removed by vacuum. The dried pellet was dissolved in phosphate buffer and analyzed by SDS-PAGE to obtain a single 25 kd band.

A 39-amino acid N-terminal segment of the purified protein was sequenced and 95% of the total proteins were shown to be mature protein. The remaining 5% contains the additional 6 amino acids of proapoAI sequence.

The purified apoAI was used to complex with repurified egg phosphatidylcholine (PC) obtained from Sigma Chemicals Co. (St. Louis, Mo.). The PC was dissolved in ethanol (4 mg/ml). The lipid solution (4 ml) was dried under vacuum to a thin film and hydrated with 2 ml of PBS, pH 7.4. The cloudy suspension was sonicated at 15° C. for 1 hour under a stream of nitrogen. The sonicated suspension was centrifuged at 38K rpm for 1 hour, and the supernatant which contains unilamellar and multilamellar liposomes was carefully removed.

The apoAI was incubated with the PC liposomes in a weight ratio of 1:5 at 37° C. for 1 hour. After incubation, apoAI bound to liposomes was separated from free apoAI by gel filtration on 10% Agarose column. This material was then analyzed by negative-stain electron microscopy.

Figure 16:
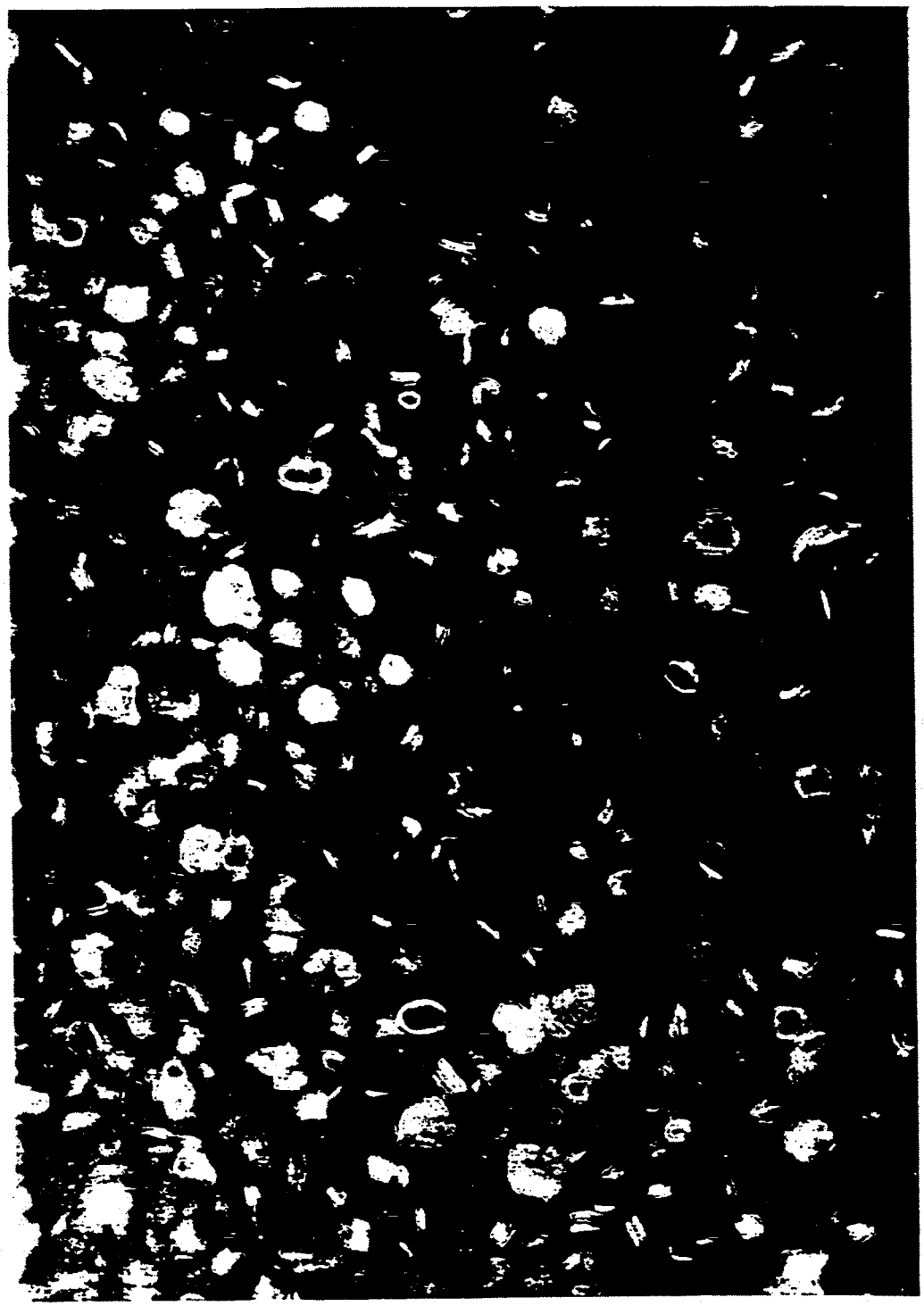
FIG. 16 is an electron micrograph of the complex formed by apoAI from transformants with phosphatidyl choline.

FIG. 16 shows (a) the many disc-like structures which have formed in the presence of AI, and (b) lack of identifiable lamellar vesicle structure. The disc-like structures are similar in appearance to nascent HDL-like particles isolated from liver perfusate (see Hamilton, R. L., et al, supra).

The ability of the purified apoAI to stabilize emulsions in serum was verified as follows. The emulsion was mixed with protein AI purified as above at a wt ratio of 100:2 mg emulsion lipid/mg AI. The mixture was incubated with shaking at 37° C. for 1 hour, to bind apoAI to the emulsion. Unbound apoAI was removed by centrifugation.

Serum from rats treated with turpentine (5 ml/kg) or from control rats treated with saline were used. In each test, 180 μl of serum was incubated with 20 μl of lipid emulsion for 2 hours at 37° C. with gentle shaking. After incubation, lipid-particle diameters were determined by laser light scattering using a sub-micron particle analyzer with optional size distribution processor analysis and multiple scattering angle detection (Coulter Model N4, Hialeah, Fla.).

The lipid emulsion without apoAI was unstable in serum from rats treated with turpentine and showed a bimodal distribution of sizes centered around 200 and 500 nm. In contrast, the emulsion containing apoAI showed no significant size change on exposure to serum obtained from turpentine-treated animals. Both emulsions were size stable in serum from control rats.

D.5.d. Atrial Naturetic Factor

CHO cells transformed with pMT'-ANF in a manner similar to that described above are verified to produce ANF when cultured in Harris F-12 medium supplemented with 10% fetal calf serum using radioimmunoassay and radiolabeling with $^{35}S$ methionine. In the $^{35}S$-methionine assay, bands appear at 18 kd and 10 kd representing pro-ANF and a fragment thereof. An isolated colony showing this production, designated CHO-8/2-81 was deposited with ATCC on 9 Apr. 1985 and has accession no. CRL-8782.

The ANF per se may be produced from the 18 kD pro-ANF by limited proteolysis using trypsin or kallikrein, as described in Currie et al (*Proc Natl Acad Sci (USA)* (1984) 81:1230–1233).

D.5.e. Erythropoietin

Each of the plasmids pMT-Epo, pEpo-SV(10), pEpo'-SV(10) and pEpo-MT were used to transform CHO cells as described above for the alternate constructions in the paragraphs above. Epo production levels were assessed by assaying the medium according to the method of Krystal, G., *Exp Hematol* (1983) 11:649–660, which employs tritiated thymidine uptake into spleen cells from phenylhydrazine-treated mice. (One mg of protein is believed to give 70,000 international units of activity.)

Pools containing pEpo-SV(10) transformants produced Epo at levels about ten-fold greater than those transformed with pMT-Epo under the same conditions though both were low producers: 8 IU/ml (0.1 μg/ml), as opposed to 0.5 IU/ml (0.01 μg/ml). Pools of cells transformed with the plasmid containing the altered gene, pEpo'-SV(10) produced 2080 IU/ml (30 μg/ml).

Cells transformed with pEpo-MT but not selected for cadmium resistance, produced Epo at the same level as those transformed with pMT-Epo; however when preselected for resistance at 5 μM Cd+ (as described for hGH in ¶D.5.a), a five-fold increase in expression was obtained. In addition, $Cd^{+2}$ resistance could be used to select for successful transformants in conjunction with pSV2-NEO. Cells which were treated with 2 μg or 10 μg, respectively, of pUC9-MT along with 15 μg pEpo-SV(10) and 1.5 μg pSV2-NEO were selectable for $Cd^{+2}$-resistant clones directly.

D.5.f. Renin

Plate Assay

Pools of CHO cells selected for G418 resistance after transformation with pMT-PPRen produce renin after induction with $5 \times 10^{-5}$ zinc sulfate and $10^{-6}M$ dexamethasone at levels of 0.02–0.2 μg/ml. The renin so produced was shown to be glycosylated by comparison of SDS gels run on $^{35}S$ methionine-labeled secreted renin with and without treatment with endo F.

By appropriate selection, much higher levels of renin production can be achieved. In one approach, cells from the transformant pool were plated out in the presence of $5 \times 10^{-5}M$ zinc sulfate in serum-free medium, and colonies which grew under these conditions were picked, expanded in serum-containing medium, and then assayed for renin production under standard induction conditions as described above. The highest renin-producing clones obtained after this process produced an average of 0.8 μg/ml, and one clone of this class, designated CBI-2B5, is described in U.S. Ser. No. 719,414, filed 3 Apr. 1985, assigned to the same assignee, and incorporated herein by reference. CBI-2B5 is deposited at ATCC with accession no. CRL 8758.

In a second approach, the cells from the pool were plated and replicated onto a polyester sheet. The replica sheet was then placed against a nitrocellulose filter for binding of the secreted cell protein. The filter was then reacted with antiprorenin antiserum followed by treating with $^{125}I$ protein A. Clones which appeared to have the highest levels of renin secretion according to this assay were picked, expanded in serum-containing medium, and reassayed for activity under standard conditions. Clones were obtained producing 1–4 μg/ml of renin, and only one such clone, arbitrarily chosen, CBI-AA2, was selected for study under production conditions, as described below.

Production Runs

The CHO transformant cells designated CBI-AA2 were prepared for roller bottle culture growth in 100 mm tissue culture dishes containing 10 ml complete media (10% FCS in F12/DMEM21 and containing 50 U/ml penicillin, 50 μg/ml streptomycin, or 400 μg/ml G-418. The cells are grown until attached (30 min), the media withdrawn, and cells refed with fresh complete media. The cells were allowed to grow to confluence, and passaged by trypsin using standard protocols for expansion. 850-cm square roller bottles were seeded with cells from one confluent flask ($4 \times 10^7$ cells) in 200 ml complete medium supplemented with 10 mM Hepes, pH 7.2. The cells were grown at 37° C. with rotation until confluent.

To induce production of renin in serum-free medium, the complete media were aspirated from the roller bottles and the cells were washed with 200 ml DMEM21. The cells were then fed with approximately 100–200 ml serum-free induction medium (SFIM). SFIM consists of F12/DMEM21 (1:1), containing 1 mM Hepes, $3 \times 10^{-5}$M FeSO$_4$, $5 \times 10^{-5}$M ZnSO$_4$, and $10^{-6}$M dexamethasone. The cells are refed with SFIM on a cycle determined by the amount of secreted protein—i.e., when approximately 100 μg/ml total protein has been secreted, as determined by Bradford assay. In general this level of total protein production occurs in approximately 2 days. CBI-AA2 showed renin production levels of 1 μg/ml or approximately 0.5 μg/ml/day.

We claim:

1. A regulatable expression system for a desired coding sequence, which system comprise Chinese Hamster Ovary (CHO) host cells in defined medium, which cells have been transformed with a DNA sequence comprising the metallothionein II (MT-II) promoter operably linked to said desired coding sequence, said medium being free of serum and further containing non-toxic metal ions and an induction mediator selected from the group consisting of iron ion and an iron-containing protein which is not a protein supplement.

2. The system of claim 1 wherein the DNA sequence further includes an enhancer operably linked to the promoter.

3. The system of claim 2 wherein the enhancer is a viral enhancer.

4. The system of claim 3 wherein the enhancer is derived from SV40.

5. The system of claim 1 wherein the cells have been cotransformed with an amplifiable toxin-resistance conferring gene.

6. The system of claim 5 wherein the coding sequence encodes a protein selected from the group consisting of alveolar surfactant protein (ASP), human growth hormone (hGH), atrial natriuretic factor (ANF), and erythropoietin (Epo).

7. The system of claim 5 wherein the toxin-resistance conferring gene is the MT gene.

8. The system of claim 7 wherein the transformed cells are resistant to cadmium ion.

9. The system of claim 8 wherein the cells are resistant to 20 μm cadmium ion.

10. The system of claim 2 wherein the cells have been cotransformed with an amplifiable toxin-resistance conferring gene.

11. The system of claim 10 wherein the toxin-resistance conferring gene is the MT gene.

12. The system of claim 11 wherein the transformed cells are resistant to cadmium ion.

13. The system of claim 12 wherein the cells are resistant to 20 μm cadmium ion.

14. The system of claim 10 wherein the coding sequence encodes a protein selected from the group consisting of alveolar surfactant protein (ASP), human growth hormone (hGH), atrial natriuretic factor (ANF), and erythropoietin (Epo).

15. The system of claim 2 wherein the coding sequence encodes a protein selected from the group consisting of alveolar surfactant protein (ASP), human growth hormone (hGH), atrial natriuretic factor (ANF), and erythropoietin (Epo).

16. The system of claim 1 wherein the MT-II is human MT-II.

17. The system of claim 1 wherein the induction mediator is iron ion or transferrin.

18. The system of claim 1 wherein the non-toxic metal ions are zinc ions in a concentration range of $2 \times 10^{-5}$ to $2 \times 10^{-4}$ M.

19. The system of claim 1 wherein the coding sequence encodes a protein selected from the group consisting of alveolar surfactant protein (ASP), human growth hormone (hGH), atrial natriuretic factor (ANF), and erythropoietin (Epo).

20. The system of claim 19 wherein the transformed host cells are CBI-37.

21. A regulatable system for expression of a desired coding sequence which comprises mammalian host cells in serum-free medium, which cells have been transformed with a DNA sequence comprising the MT-II promoter operably linked to a desired coding sequence, wherein said serum-free medium is supplemented with an effective amount of an induction mediator selected from the group consisting of iron ion and an iron-containing protein which is not a protein supplement.

22. The system of claim 21 wherein the induction mediator is >5 μg/ml human transferrin or $1-3 \times 10^{-5}$M iron ion.

23. The system of claim 21 wherein the cells have been cotransformed with an amplifiable toxin-resistance conferring gene.

24. The system of claim 23 wherein the toxin-resistance conferring gene is the MT gene.

25. The system of claim 21 wherein the induction mediator is iron ion or transferrin.

26. The system of claim 21 wherein the DNA sequence further includes an enhancer operably linked to the promoter.

27. The system of claim 26 wherein the enhancer is a viral enhancer.

28. The system of claim 26 wherein the cells have been cotransformed with an amplifiable toxin-resistance conferring gene.

29. The system of claim 28 wherein the toxin-resistance conferring gene is the MT gene.

30. A method for obtaining regulatable expression of a desired coding sequence in mammalian host cells, said method comprising inducing the host cells which have been transformed with a DNA sequence comprising the MT-II promoter operably linked to the desired coding sequence, in serum-free medium with an effective amount of an induction mediator selected from the group consisting of iron ion and an iron-containing protein which is not a protein supplement, by adding an effective amount of zinc ion.

31. The method of claim 30 wherein the DNA sequence further includes an enhancer operably linked to the promoter.

32. The method of claim 31 wherein the host cells have been cotransformed with an amplifiable toxin resistance-conferring gene.

33. The method of claim 30 wherein the host cells have been cotransformed with an amplifiable toxin resistance-conferring gene.

34. The method of claim 30 wherein said cells are induced by addition of an effective amount of zinc ion.

35. The method of claim 30 wherein the induction mediator is iron ion or transferrin.

36. A regulatable system for expression of a desired coding sequence which comprises mammalian host cells transformed with a DNA sequence comprising the MT-II promoter operably linked to a desired coding sequence, in contact with a serum-free medium supplemented with an effective amount of an induction mediator selected from the group consisting of iron ion and an iron-containing protein which is not a protein supplement, and zinc ion in the range of $2\times10^{-5}$ to $2\times10^{-4}$M.

37. The system of claim 36 wherein the induction mediator is iron ion or transferrin.

* * * * *